(12) United States Patent
Euteneuer et al.

(10) Patent No.: US 10,245,138 B2
(45) Date of Patent: Apr. 2, 2019

(54) METHODS AND APPARATUS FOR DELIVERING AND POSITIONING SHEET-LIKE MATERIALS IN SURGERY

(71) Applicant: Rotation Medical, Inc., Plymouth, MN (US)

(72) Inventors: Charles L. Euteneuer, St. Michael, MN (US); Nathaniel Z. Zenz-Olson, Blaine, MN (US); John Quackenbush, North Oaks, MN (US); Jeff Sims, Apple Valley, MN (US)

(73) Assignee: Rotation Medical, Inc., Plymouth, MN (US)

( * ) Notice: Subject to any disclaimer, the term of this patent is extended or adjusted under 35 U.S.C. 154(b) by 290 days.

(21) Appl. No.: 14/939,517

(22) Filed: Nov. 12, 2015

(65) Prior Publication Data
US 2016/0058535 A1     Mar. 3, 2016

Related U.S. Application Data

(63) Continuation of application No. 13/889,757, filed on May 8, 2013, now Pat. No. 9,314,331, which is a
(Continued)

(51) Int. Cl.
*A61F 2/08*     (2006.01)
*A61F 2/00*     (2006.01)
(Continued)

(52) U.S. Cl.
CPC ............ *A61F 2/0805* (2013.01); *A61B 90/39* (2016.02); *A61F 2/0063* (2013.01);
(Continued)

(58) Field of Classification Search
CPC ........ A61F 2/0805; A61F 2/0063; A61F 2/08; A61F 2/04; A61F 2/02; A61F 2002/0072;
(Continued)

(56) References Cited

U.S. PATENT DOCUMENTS 511,238 A    12/1893   Hieatzman et al.
765,793 A     7/1904   Ruckel
(Continued)

FOREIGN PATENT DOCUMENTS

CA    2390508 A1    5/2011
EP    0142225 A1    5/1985
(Continued)

OTHER PUBLICATIONS

Bahler et al., "Trabecular bypass stents decrease intraocular pressure in cultured himan anterior segments," AM. J. Ophthalmology, vol. 138(6), pp. 988-994, Dec. 2004.
(Continued)

*Primary Examiner* — Christopher L Templeton
*Assistant Examiner* — George J Ulsh
(74) *Attorney, Agent, or Firm* — Seager, Tufte & Wickhem LLP.

(57) ABSTRACT

An implant delivery system for delivering a sheet-like implant is disclosed. The implant delivery system includes a distal guidewire port for receiving the proximal end of guidewire after the guidewire distal end has been affixed to a first point on bone or other tissue. The implant delivery system is tracked over the guidewire to a selected position defined by the guidewire attachment. The device includes an implant spreader assembly disposed proximate the distal end of a delivery shaft. The implant spreader assembly includes a first arm and a second arm. The arms are coupled to the delivery shaft such that the first arm and second arm are moveable between a closed position and an open position. When pivoting to the open position the distal end of each arm travels in a generally transverse direction to spread a sheet-like implant.

20 Claims, 33 Drawing Sheets

Related U.S. Application Data continuation of application No. 13/722,796, filed on Dec. 20, 2012, now Pat. No. 9,198,751.

(60) Provisional application No. 61/581,628, filed on Dec. 29, 2011.

(51) Int. Cl.
    *A61F 2/40* (2006.01)
    *A61B 90/00* (2016.01)

(52) U.S. Cl.
    CPC .............. *A61F 2/0811* (2013.01); *A61F 2/40* (2013.01); *A61B 2090/061* (2016.02); *A61B 2090/0817* (2016.02); *A61B 2090/3908* (2016.02); *A61B 2090/3937* (2016.02); *A61F 2/08* (2013.01); *A61F 2002/0072* (2013.01); *A61F 2002/0864* (2013.01); *F04C 2270/0421* (2013.01)

(58) Field of Classification Search
    CPC .. A61F 2/1664; A61F 2/40; A61B 2017/1778; A61B 2017/1125; A61B 17/28; A61B 17/29; A61B 2017/0488; A61B 17/128; A61B 17/1285; A61B 17/8866; A61B 2017/081; A61B 2017/1103; A61B 2019/461; A61B 2019/4889
    USPC .................................................. 606/151, 279
    See application file for complete search history.

(56) References Cited

U.S. PATENT DOCUMENTS

| | | |
|---|---|---|
| 1,728,316 A | 9/1929 | von Wechenfeldt et al. |
| 1,855,546 A | 4/1932 | File |
| 1,868,100 A | 7/1932 | Goodstein |
| 1,910,688 A | 5/1933 | Goodstein |
| 1,940,351 A | 12/1933 | Howard |
| 2,034,785 A | 3/1936 | Wappler |
| 2,075,508 A | 3/1937 | Davidson |
| 2,131,321 A | 9/1938 | Hart |
| 2,158,242 A | 5/1939 | Maynard |
| 2,199,025 A | 4/1940 | Conn |
| 2,201,610 A | 5/1940 | Dawson, Jr. |
| 2,254,620 A | 9/1941 | Miller |
| 2,277,931 A | 3/1942 | Moe |
| 2,283,814 A | 5/1942 | La Place |
| 2,316,297 A | 4/1943 | Southerland et al. |
| 2,421,193 A | 5/1947 | Gardner |
| 2,571,813 A | 10/1951 | Austin |
| 2,630,316 A | 3/1953 | Foster |
| 2,684,070 A | 7/1954 | Kelsey |
| 2,744,251 A | 5/1956 | Vollmer |
| 2,790,341 A | 4/1957 | Keep et al. |
| 2,817,339 A | 12/1957 | Sullivan |
| 2,825,162 A | 3/1958 | Flood |
| 2,881,762 A | 4/1959 | Lowrie |
| 2,910,067 A | 10/1959 | White |
| 3,068,870 A | 12/1962 | Levin |
| 3,077,812 A | 2/1963 | Dietrich |
| 3,103,666 A | 9/1963 | Bone |
| 3,123,077 A | 3/1964 | Alcamo |
| 3,209,754 A | 10/1965 | Brown |
| 3,221,746 A | 12/1965 | Noble |
| 3,470,834 A | 10/1969 | Bone |
| 3,527,223 A | 9/1970 | Shein |
| 3,570,497 A | 3/1971 | Lemole |
| 3,577,837 A | 5/1971 | Bader, Jr. |
| 3,579,831 A | 5/1971 | Stevens et al. |
| 3,643,851 A | 2/1972 | Green et al. |
| 3,687,138 A | 8/1972 | Jarvik |
| 3,716,058 A | 2/1973 | Tanner, Jr. |
| 3,717,294 A | 2/1973 | Green |
| 3,757,629 A | 9/1973 | Schneider |
| 3,777,538 A | 12/1973 | Weatherly et al. |
| 3,837,555 A | 9/1974 | Green |
| 3,845,772 A | 11/1974 | Smith |
| 3,875,648 A | 4/1975 | Bone |
| 3,960,147 A | 6/1976 | Murray |
| 3,976,079 A | 8/1976 | Samuels et al. |
| 4,014,492 A | 3/1977 | Rothfuss |
| 4,127,227 A | 11/1978 | Green |
| 4,259,959 A | 4/1981 | Walker |
| 4,263,903 A | 4/1981 | Griggs |
| 4,265,226 A | 5/1981 | Cassimally |
| 4,317,451 A | 3/1982 | Cerwin et al. |
| 4,400,833 A | 8/1983 | Kurland |
| 4,422,567 A | 12/1983 | Haynes |
| 4,454,875 A | 6/1984 | Pratt et al. |
| 4,480,641 A | 11/1984 | Failla et al. |
| 4,485,816 A | 12/1984 | Krumme |
| 4,526,174 A | 7/1985 | Froehlich |
| 4,549,545 A | 10/1985 | Levy |
| 4,570,623 A | 2/1986 | Ellison et al. |
| 4,595,007 A | 6/1986 | Mericle |
| 4,624,254 A | 11/1986 | McGarry et al. |
| 4,627,437 A | 12/1986 | Bedi et al. |
| 4,632,100 A | 12/1986 | Somers et al. |
| 4,635,637 A | 1/1987 | Schreiber |
| 4,669,473 A | 6/1987 | Richards et al. |
| 4,696,300 A | 9/1987 | Anderson |
| 4,719,917 A | 1/1988 | Barrows et al. |
| 4,738,255 A | 4/1988 | Goble et al. |
| 4,741,330 A | 5/1988 | Hayhurst |
| 4,762,260 A | 8/1988 | Richards et al. |
| 4,799,495 A | 1/1989 | Hawkins et al. |
| 4,809,695 A | 3/1989 | Gwathmey et al. |
| 4,851,005 A | 7/1989 | Hunt et al. |
| 4,858,608 A | 8/1989 | McQuilkin |
| 4,884,572 A | 12/1989 | Bays et al. |
| 4,887,601 A | 12/1989 | Richards |
| 4,924,866 A | 5/1990 | Yoon |
| 4,930,674 A | 6/1990 | Barak |
| 4,968,315 A | 11/1990 | Gattuma |
| 4,976,715 A | 12/1990 | Bays et al. |
| 4,994,073 A | 2/1991 | Green |
| 4,997,436 A | 3/1991 | Oberlander |
| 5,002,563 A | 3/1991 | Pyka et al. |
| 5,013,316 A | 5/1991 | Goble et al. |
| 5,015,249 A | 5/1991 | Nakao et al. |
| 5,037,422 A | 8/1991 | Hayhurst et al. |
| 5,041,129 A | 8/1991 | Hayhurst et al. |
| 5,046,513 A | 9/1991 | Gattuma et al. |
| 5,053,047 A | 10/1991 | Yoon |
| 5,059,206 A | 10/1991 | Winters |
| 5,062,563 A | 11/1991 | Green et al. |
| 5,100,417 A | 3/1992 | Cerier et al. |
| 5,102,421 A | 4/1992 | Anspach, Jr. |
| 5,116,357 A | 5/1992 | Eberbach |
| 5,122,155 A | 6/1992 | Eberbach |
| 5,123,913 A | 6/1992 | Wilk et al. |
| RE34,021 E | 8/1992 | Mueller et al. |
| 5,141,515 A | 8/1992 | Eberbach |
| 5,141,520 A | 8/1992 | Goble et al. |
| 5,156,609 A | 10/1992 | Nakao et al. |
| 5,156,616 A | 10/1992 | Meadows et al. |
| 5,167,665 A | 12/1992 | McKinney |
| 5,171,259 A | 12/1992 | Inoue |
| 5,174,295 A | 12/1992 | Christian et al. |
| 5,174,487 A | 12/1992 | Rothfuss et al. |
| 5,176,682 A | 1/1993 | Chow |
| 5,176,692 A | 1/1993 | Wilk et al. |
| 5,203,787 A | 4/1993 | Noblitt et al. |
| 5,217,472 A | 6/1993 | Green et al. |
| 5,224,946 A | 7/1993 | Hayhurst et al. |
| 5,242,457 A | 9/1993 | Akopov et al. |
| 5,246,441 A | 9/1993 | Ross et al. |
| 5,251,642 A | 10/1993 | Handlos |
| 5,261,914 A | 11/1993 | Warren |
| 5,269,753 A | 12/1993 | Wilk |
| 5,269,783 A | 12/1993 | Sander |
| 5,282,829 A | 2/1994 | Hermes |
| 5,289,963 A | 3/1994 | McGarry et al. |

(56) References Cited

U.S. PATENT DOCUMENTS

| | | |
|---|---|---|
| 5,290,217 A | 3/1994 | Campos |
| 5,304,187 A | 4/1994 | Green et al. |
| 5,333,624 A | 8/1994 | Tovey |
| 5,342,396 A | 8/1994 | Cook |
| 5,350,400 A | 9/1994 | Esposito et al. |
| 5,352,229 A | 10/1994 | Goble et al. |
| 5,354,292 A | 10/1994 | Braeuer et al. |
| 5,364,408 A | 11/1994 | Gordon |
| 5,366,460 A | 11/1994 | Eberbach |
| 5,370,650 A | 12/1994 | Tovey et al. |
| 5,372,604 A | 12/1994 | Trott |
| 5,380,334 A | 1/1995 | Torrie et al. |
| 5,383,477 A | 1/1995 | DeMatteis |
| 5,397,332 A | 3/1995 | Kammerer et al. |
| 5,403,326 A | 4/1995 | Harrison et al. |
| 5,405,360 A | 4/1995 | Tovey |
| 5,411,522 A | 5/1995 | Trott |
| 5,411,523 A | 5/1995 | Goble |
| 5,417,691 A | 5/1995 | Hayhurst |
| 5,417,712 A | 5/1995 | Whittaker et al. |
| 5,425,490 A | 6/1995 | Goble et al. |
| 5,441,502 A | 8/1995 | Bartlett |
| 5,441,508 A | 8/1995 | Gazielly et al. |
| 5,456,720 A | 10/1995 | Schultz et al. |
| 5,464,403 A | 11/1995 | Kieturakis et al. |
| 5,478,354 A | 12/1995 | Tovey et al. |
| 5,486,197 A | 1/1996 | Le et al. |
| 5,497,933 A | 3/1996 | DeFonzo et al. |
| 5,500,000 A | 3/1996 | Feagin et al. |
| 5,501,695 A | 3/1996 | Anspach, Jr. et al. |
| 5,503,623 A | 4/1996 | Tilton, Jr. |
| 5,505,735 A | 4/1996 | Li |
| 5,507,754 A | 4/1996 | Green et al. |
| 5,520,700 A | 5/1996 | Beyar et al. |
| 5,522,817 A | 6/1996 | Sander et al. |
| 5,545,180 A | 8/1996 | Le et al. |
| 5,560,532 A | 10/1996 | DeFonzo et al. |
| 5,562,689 A | 10/1996 | Green et al. |
| 5,569,306 A | 10/1996 | Thal |
| 5,582,616 A | 12/1996 | Bolduc et al. |
| 5,584,835 A | 12/1996 | Greenfield |
| 5,618,314 A | 4/1997 | Harwin et al. |
| 5,622,257 A | 4/1997 | Deschenes et al. |
| 5,628,751 A | 5/1997 | Sander et al. |
| 5,643,319 A | 7/1997 | Green et al. |
| 5,643,321 A | 7/1997 | McDevitt |
| 5,647,874 A | 7/1997 | Hayhurst |
| 5,649,963 A | 7/1997 | McDevitt |
| 5,662,683 A | 9/1997 | Kay |
| 5,667,513 A | 9/1997 | Torrie et al. |
| 5,674,245 A | 10/1997 | Ilgen |
| 5,681,342 A | 10/1997 | Benchetrit |
| 5,702,215 A | 12/1997 | Li |
| 5,713,903 A | 2/1998 | Sander et al. |
| 5,720,753 A | 2/1998 | Sander et al. |
| 5,725,541 A | 3/1998 | Anspach, III et al. |
| 5,741,282 A | 4/1998 | Anspach, III et al. |
| 5,766,246 A | 6/1998 | Mulhauser et al. |
| 5,782,864 A | 7/1998 | Lizardi |
| 5,797,909 A | 8/1998 | Michelson |
| 5,797,931 A | 8/1998 | Bito et al. |
| 5,797,963 A | 8/1998 | McDevitt |
| 5,807,403 A | 9/1998 | Beyar et al. |
| 5,830,221 A | 11/1998 | Stein et al. |
| 5,836,961 A | 11/1998 | Kieturakis et al. |
| 5,868,762 A | 2/1999 | Cragg et al. |
| 5,873,891 A | 2/1999 | Sohn |
| 5,885,258 A | 3/1999 | Sachdeva et al. |
| 5,885,294 A | 3/1999 | Pedlick et al. |
| 5,893,856 A | 4/1999 | Jacob et al. |
| 5,904,696 A | 5/1999 | Rosenman |
| 5,919,184 A | 7/1999 | Tilton, Jr. |
| 5,922,026 A | 7/1999 | Chin |
| 5,928,244 A | 7/1999 | Tovey et al. |
| 5,948,000 A | 9/1999 | Larsen et al. |
| 5,957,939 A | 9/1999 | Heaven et al. |
| 5,957,953 A | 9/1999 | DiPoto et al. |
| 5,968,044 A | 10/1999 | Nicholson et al. |
| 5,980,557 A | 11/1999 | Iserin et al. |
| 5,989,265 A | 11/1999 | Bouquet De La Joliniere et al. |
| 5,997,552 A | 12/1999 | Person et al. |
| 6,063,088 A | 5/2000 | Winslow |
| 6,099,518 A | 8/2000 | Adams et al. |
| 6,156,045 A | 12/2000 | Ulbrich et al. |
| 6,179,840 B1 | 1/2001 | Bowman |
| 6,193,731 B1 | 2/2001 | Oppelt et al. |
| 6,193,733 B1 | 2/2001 | Adams |
| 6,245,072 B1 | 6/2001 | Zdeblick et al. |
| 6,302,885 B1 | 10/2001 | Essiger |
| 6,312,442 B1 | 11/2001 | Kieturakis et al. |
| 6,315,789 B1 | 11/2001 | Cragg |
| 6,318,616 B1 | 11/2001 | Pasqualucci et al. |
| 6,322,563 B1 | 11/2001 | Cummings et al. |
| 6,325,805 B1 | 12/2001 | Ogilvie et al. |
| 6,387,113 B1 | 5/2002 | Hawkins et al. |
| 6,391,333 B1 | 5/2002 | Li et al. |
| 6,413,274 B1 | 7/2002 | Pedros |
| 6,425,900 B1 | 7/2002 | Knodel et al. |
| 6,436,110 B2 | 8/2002 | Bowman et al. |
| 6,447,522 B2 | 9/2002 | Gambale et al. |
| 6,447,524 B1 | 9/2002 | Knodel et al. |
| 6,478,803 B1 | 11/2002 | Kapec et al. |
| 6,482,178 B1 | 11/2002 | Andrews et al. |
| 6,482,210 B1 | 11/2002 | Skiba et al. |
| 6,506,190 B1 | 1/2003 | Walshe |
| 6,511,499 B2 | 1/2003 | Schmieding et al. |
| 6,517,564 B1 | 2/2003 | Grafton et al. |
| 6,524,316 B1 | 2/2003 | Nicholson et al. |
| 6,527,795 B1 | 3/2003 | Lizardi |
| 6,530,933 B1 | 3/2003 | Yeung et al. |
| 6,540,769 B1 | 4/2003 | Miller, III |
| 6,551,333 B2 | 4/2003 | Kuhns et al. |
| 6,554,852 B1 | 4/2003 | Oberlander |
| 6,569,186 B1 | 5/2003 | Winters et al. |
| 6,575,976 B2 | 6/2003 | Grafton |
| 6,599,289 B1 | 7/2003 | Bojarski et al. |
| 6,620,185 B1 | 9/2003 | Harvie et al. |
| 6,629,988 B2 | 10/2003 | Weadock |
| 6,638,297 B1 | 10/2003 | Huitema |
| 6,648,893 B2 | 11/2003 | Dudasik |
| 6,666,872 B2 | 12/2003 | Barreiro et al. |
| 6,673,094 B1 | 1/2004 | McDevitt et al. |
| 6,685,728 B2 | 2/2004 | Sinnott et al. |
| 6,692,506 B1 | 2/2004 | Ory et al. |
| 6,723,099 B1 | 4/2004 | Goshert |
| 6,726,704 B1 | 4/2004 | Loshakove et al. |
| 6,726,705 B2 | 4/2004 | Peterson et al. |
| 6,740,100 B2 | 5/2004 | Demopulos et al. |
| 6,746,472 B2 | 6/2004 | Frazier et al. |
| 6,764,500 B1 | 7/2004 | Van De Moer et al. |
| 6,770,073 B2 | 8/2004 | McDevitt et al. |
| 6,779,701 B2 | 8/2004 | Bailly et al. |
| 6,800,081 B2 | 10/2004 | Parodi |
| 6,835,206 B2 | 12/2004 | Jackson |
| 6,849,078 B2 | 2/2005 | Durgin et al. |
| 6,887,259 B2 | 5/2005 | Lizardi |
| 6,926,723 B1 | 8/2005 | Mulhauser et al. |
| 6,932,834 B2 | 8/2005 | Lizardi et al. |
| 6,939,365 B1 | 9/2005 | Fogarty et al. |
| 6,946,003 B1 | 9/2005 | Wolowacz et al. |
| 6,949,117 B2 | 9/2005 | Gambale et al. |
| 6,964,685 B2 | 11/2005 | Murray et al. |
| 6,966,916 B2 | 11/2005 | Kumar |
| 6,972,027 B2 | 12/2005 | Fallin et al. |
| 6,984,241 B2 | 1/2006 | Lubbers et al. |
| 6,991,597 B2 | 1/2006 | Gellman et al. |
| 7,008,435 B2 | 3/2006 | Cummins |
| 7,021,316 B2 | 4/2006 | Leiboff |
| 7,025,772 B2 | 4/2006 | Gellman et al. |
| 7,033,379 B2 | 4/2006 | Peterson |
| 7,037,324 B2 | 5/2006 | Martinek |
| 7,048,171 B2 | 5/2006 | Thornton et al. |
| 7,063,711 B1 | 6/2006 | Loshakove et al. |
| 7,083,638 B2 | 8/2006 | Foerster |

(56) References Cited

U.S. PATENT DOCUMENTS

| | | |
|---|---|---|
| 7,087,064 B1 | 8/2006 | Hyde |
| 7,112,214 B2 | 9/2006 | Peterson et al. |
| 7,118,581 B2 | 10/2006 | Fridén |
| 7,144,413 B2 | 12/2006 | Wilford et al. |
| 7,144,414 B2 | 12/2006 | Harvie et al. |
| 7,150,750 B2 | 12/2006 | Damarati |
| 7,153,314 B2 | 12/2006 | Laufer et al. |
| 7,160,314 B2 | 1/2007 | Sgro et al. |
| 7,160,326 B2 | 1/2007 | Ball |
| 7,163,551 B2 | 1/2007 | Anthony et al. |
| 7,163,563 B2 | 1/2007 | Schwartz et al. |
| 7,169,157 B2 | 1/2007 | Kayan |
| 7,189,251 B2 | 3/2007 | Kay |
| 7,201,754 B2 | 4/2007 | Stewart et al. |
| 7,214,232 B2 | 5/2007 | Bowman et al. |
| 7,226,469 B2 | 6/2007 | Benavitz et al. |
| 7,229,452 B2 | 6/2007 | Kayan |
| 7,247,164 B1 | 7/2007 | Ritchart et al. |
| 7,303,577 B1 | 12/2007 | Dean |
| 7,309,337 B2 | 12/2007 | Colleran et al. |
| 7,320,692 B1 | 1/2008 | Bender et al. |
| 7,320,701 B2 | 1/2008 | Haut et al. |
| 7,322,935 B2 | 1/2008 | Palmer et al. |
| 7,326,231 B2 | 2/2008 | Phillips et al. |
| 7,343,920 B2 | 3/2008 | Toby et al. |
| 7,368,124 B2 | 5/2008 | Chun et al. |
| 7,377,934 B2 | 5/2008 | Lin et al. |
| 7,381,213 B2 | 6/2008 | Lizardi |
| 7,390,329 B2 | 6/2008 | Westra et al. |
| 7,399,304 B2 | 7/2008 | Gambale et al. |
| 7,404,824 B1 | 7/2008 | Webler et al. |
| 7,416,554 B2 | 8/2008 | Lam et al. |
| 7,452,368 B2 | 11/2008 | Liberatore et al. |
| 7,460,913 B2 | 12/2008 | Kuzma et al. |
| 7,463,933 B2 | 12/2008 | Wahlstrom et al. |
| 7,465,308 B2 | 12/2008 | Sikora et al. |
| 7,481,832 B1 | 1/2009 | Meridew et al. |
| 7,485,124 B2 | 2/2009 | Kuhns et al. |
| 7,497,854 B2 | 3/2009 | Gill et al. |
| 7,500,972 B2 | 3/2009 | Voegele et al. |
| 7,500,980 B2 | 3/2009 | Gill et al. |
| 7,500,983 B1 | 3/2009 | Kaiser et al. |
| 7,503,474 B2 | 3/2009 | Hillstead et al. |
| 7,506,791 B2 | 3/2009 | Omaits et al. |
| 7,559,941 B2 | 7/2009 | Zannis et al. |
| 7,572,276 B2 | 8/2009 | Lim et al. |
| 7,585,311 B2 | 9/2009 | Green et al. |
| 7,766,208 B2 | 8/2010 | Epperly et al. |
| 7,771,440 B2 | 8/2010 | Ortiz et al. |
| 7,776,057 B2 | 8/2010 | Laufer et al. |
| 7,780,685 B2 | 8/2010 | Hunt et al. |
| 7,785,255 B2 | 8/2010 | Malkani |
| 7,807,192 B2 | 10/2010 | Li et al. |
| 7,819,880 B2 | 10/2010 | Zannis et al. |
| 7,918,879 B2 | 4/2011 | Yeung et al. |
| 8,114,101 B2 | 2/2012 | Criscuolo et al. |
| 8,197,837 B2 | 6/2012 | Jamiolkowski et al. |
| 9,113,977 B2 | 8/2015 | Euteneuer et al. |
| 9,125,650 B2 | 9/2015 | Euteneuer et al. |
| 9,204,940 B2 | 12/2015 | Euteneuer et al. |
| 9,393,103 B2 | 7/2016 | Van Kampen et al. |
| 2002/0077687 A1 | 6/2002 | Ahn |
| 2002/0090725 A1 | 7/2002 | Simpson et al. |
| 2002/0123767 A1 | 9/2002 | Prestel |
| 2002/0165559 A1 | 11/2002 | Grant et al. |
| 2003/0073979 A1 | 4/2003 | Naimark et al. |
| 2003/0125748 A1 | 7/2003 | Li et al. |
| 2003/0212456 A1 | 11/2003 | Lipchitz et al. |
| 2004/0059416 A1 | 3/2004 | Murray et al. |
| 2004/0138705 A1 | 7/2004 | Heino et al. |
| 2004/0167519 A1 | 8/2004 | Weiner et al. |
| 2005/0015021 A1 | 1/2005 | Shiber |
| 2005/0049618 A1 | 3/2005 | Masuda et al. |
| 2005/0051597 A1 | 3/2005 | Toledano |
| 2005/0059996 A1 | 3/2005 | Bauman et al. |
| 2005/0060033 A1 | 3/2005 | Vacanti et al. |
| 2005/0107807 A1 | 5/2005 | Nakao |
| 2005/0113736 A1 | 5/2005 | Orr et al. |
| 2005/0171569 A1 | 8/2005 | Girard et al. |
| 2005/0187576 A1 | 8/2005 | Whitman et al. |
| 2005/0240222 A1 | 10/2005 | Shipp |
| 2005/0274768 A1 | 12/2005 | Cummins et al. |
| 2006/0074423 A1 | 4/2006 | Alleyne et al. |
| 2006/0178743 A1 | 8/2006 | Carter |
| 2006/0235442 A1 | 10/2006 | Huitema |
| 2006/0293760 A1 | 12/2006 | DeDeyne |
| 2007/0078477 A1 | 4/2007 | Heneveld, Sr. et al. |
| 2007/0083236 A1 | 4/2007 | Sikora et al. |
| 2007/0112361 A1 | 5/2007 | Schonholz et al. |
| 2007/0179531 A1 | 8/2007 | Thornes |
| 2007/0185506 A1 | 8/2007 | Jackson |
| 2007/0190108 A1 | 8/2007 | Datta et al. |
| 2007/0219558 A1 | 9/2007 | Deutsch |
| 2007/0270804 A1 | 11/2007 | Chudik |
| 2007/0288023 A1 | 12/2007 | Pellegrino et al. |
| 2008/0027470 A1 | 1/2008 | Hart et al. |
| 2008/0051888 A1 | 2/2008 | Ratcliffe et al. |
| 2008/0065153 A1 | 3/2008 | Allard et al. |
| 2008/0090936 A1 | 4/2008 | Fujimura et al. |
| 2008/0125869 A1 | 5/2008 | Paz et al. |
| 2008/0135600 A1 | 6/2008 | Hiranuma et al. |
| 2008/0173691 A1 | 7/2008 | Mas et al. |
| 2008/0188874 A1 | 8/2008 | Henderson |
| 2008/0188936 A1 | 8/2008 | Ball et al. |
| 2008/0195119 A1 | 8/2008 | Ferree |
| 2008/0200949 A1 | 8/2008 | Hiles et al. |
| 2008/0241213 A1 | 10/2008 | Chun et al. |
| 2008/0272173 A1 | 11/2008 | Coleman et al. |
| 2008/0306408 A1 | 12/2008 | Lo |
| 2009/0001122 A1 | 1/2009 | Prommersberger et al. |
| 2009/0012521 A1 | 1/2009 | Axelson, Jr. et al. |
| 2009/0030434 A1 | 1/2009 | Paz et al. |
| 2009/0069806 A1 | 3/2009 | De La Mora Levy et al. |
| 2009/0076541 A1 | 3/2009 | Chin et al. |
| 2009/0105535 A1 | 4/2009 | Green et al. |
| 2009/0112085 A1 | 4/2009 | Eby |
| 2009/0134198 A1 | 5/2009 | Knodel et al. |
| 2009/0156986 A1 | 6/2009 | Trenhaile |
| 2009/0156997 A1 | 6/2009 | Trenhaile |
| 2009/0182245 A1 | 7/2009 | Zambelli |
| 2009/0242609 A1 | 10/2009 | Kanner |
| 2010/0145367 A1 | 6/2010 | Ratcliffe |
| 2010/0147922 A1 | 6/2010 | Olson |
| 2010/0163598 A1 | 7/2010 | Belzer |
| 2010/0191332 A1 | 7/2010 | Euteneuer et al. |
| 2010/0241227 A1 | 9/2010 | Euteneuer et al. |
| 2010/0249801 A1 | 9/2010 | Sengun et al. |
| 2010/0256675 A1 | 10/2010 | Romans |
| 2010/0274278 A1 | 10/2010 | Fleenor et al. |
| 2010/0292715 A1 | 11/2010 | Nering et al. |
| 2010/0292791 A1 | 11/2010 | Lu et al. |
| 2010/0312250 A1 | 12/2010 | Euteneuer et al. |
| 2010/0312275 A1 | 12/2010 | Euteneuer et al. |
| 2010/0327042 A1 | 12/2010 | Amid et al. |
| 2011/0000950 A1 | 1/2011 | Euteneuer et al. |
| 2011/0004221 A1 | 1/2011 | Euteneuer et al. |
| 2011/0011917 A1 | 1/2011 | Loulmet |
| 2011/0034942 A1 | 2/2011 | Levin et al. |
| 2011/0040310 A1 | 2/2011 | Levin et al. |
| 2011/0040311 A1 | 2/2011 | Levin et al. |
| 2011/0066166 A1 | 3/2011 | Levin et al. |
| 2011/0106154 A1 | 5/2011 | DiMatteo et al. |
| 2011/0114700 A1 | 5/2011 | Baxter, III et al. |
| 2011/0224702 A1 | 9/2011 | Van Kampen et al. |
| 2011/0264149 A1 | 10/2011 | Pappalardo et al. |
| 2012/0100200 A1 | 4/2012 | Belcheva et al. |
| 2012/0160893 A1 | 6/2012 | Harris et al. |
| 2012/0193391 A1 | 8/2012 | Michler et al. |
| 2012/0209401 A1 | 8/2012 | Euteneuer et al. |
| 2012/0211543 A1 | 8/2012 | Euteneuer |
| 2012/0248171 A1 | 10/2012 | Bailly et al. |
| 2012/0316608 A1 | 12/2012 | Foley |
| 2013/0153627 A1 | 6/2013 | Euteneuer et al. |
| 2013/0153628 A1 | 6/2013 | Euteneuer |

(56) References Cited

U.S. PATENT DOCUMENTS

| | | |
|---|---|---|
| 2013/0158554 A1 | 6/2013 | Euteneuer et al. |
| 2013/0158587 A1 | 6/2013 | Euteneuer et al. |
| 2013/0158661 A1 | 6/2013 | Euteneuer et al. |
| 2013/0172920 A1 | 7/2013 | Euteneuer et al. |
| 2013/0172997 A1 | 7/2013 | Euteneuer et al. |
| 2013/0184716 A1 | 7/2013 | Euteneuer et al. |
| 2013/0240598 A1 | 9/2013 | Euteneuer et al. |

FOREIGN PATENT DOCUMENTS

| | | |
|---|---|---|
| EP | 0298400 A1 | 1/1989 |
| EP | 0390613 A1 | 10/1990 |
| EP | 0543499 A1 | 5/1993 |
| EP | 0548998 A1 | 6/1993 |
| EP | 0557963 A1 | 9/1993 |
| EP | 0589306 A2 | 3/1994 |
| EP | 0908152 A1 | 4/1999 |
| EP | 1491157 A1 | 12/2004 |
| EP | 1559379 A1 | 8/2005 |
| EP | 2030576 A2 | 3/2009 |
| GB | 2154688 A | 9/1985 |
| GB | 2397240 A | 7/2004 |
| JP | 58188442 A | 11/1983 |
| JP | 2005506122 A | 3/2005 |
| JP | 2006515774 A | 6/2006 |
| WO | 8505025 A1 | 11/1985 |
| WO | 0176456 A2 | 10/2001 |
| WO | 0234140 A2 | 5/2002 |
| WO | 03105670 A2 | 12/2003 |
| WO | 2004000138 A1 | 12/2003 |
| WO | 2004093690 A1 | 11/2004 |
| WO | 2005016389 A2 | 2/2005 |
| WO | 2006086679 A1 | 8/2006 |
| WO | 2007014910 A1 | 2/2007 |
| WO | 2007030676 A2 | 3/2007 |
| WO | 2007078978 A2 | 7/2007 |
| WO | 2007082088 A2 | 7/2007 |
| WO | 2008111073 A2 | 9/2008 |
| WO | 2008111078 A2 | 9/2008 |
| WO | 2008139473 A2 | 11/2008 |
| WO | 2009079211 A1 | 6/2009 |
| WO | 2009143331 A1 | 11/2009 |
| WO | 2011095890 A2 | 8/2011 |
| WO | 2011128903 A2 | 10/2011 |

OTHER PUBLICATIONS

Chamay et al., "Digital contracture deformity after implantation of a silicone prosthesis: Light and electron microscopic study," The Journal of Hand Surgery, vol. 3(3), pp. 266-270, May 1978.

D'Ermo et al., "Our Results with the operation of ab externo," Ophthalmologica, vol. 168, pp. 347-355, (year of pub. sufficiently earlier than effective US filing date and any foreign priority date) 1971.

France et al., "Biomechanical evaluation of rotator cuff fixation methods," The American Journal of Sports Medicine, vol. 17(2), pp. 176-181, Mar.-Apr. 1989.

Goodship et al., "An assessment of filamentous carbon fibre for the treatment of tendon injury in the horse," Veterinary Record, vol. 17(2) pp. 217-221, Mar. 8, 1980.

Hunter et al., "Flexor-tendon reconstruction in severely damaged hands," The Journal of Bone and Join Surgery (American Volume), voo.54-A(5), pp. 329-358, Jul. 1971.

Johnstone et al., "Microsurgery of Schlemm's Canal and the human aqueous outflow system," Am. J. Ophthalmology, vol. 76(6), pp. 906-917, Dec. 1973.

Kowalsky et al., "Evaluation of suture abrasion against rotator cuff tendon and proximal humerus bone," Arthroscopy, The Journal of Arthoscopic and Related Surgery, vol. 24(3), pp. 329-334, Mar. 2008.

Lee et al., "Aqueous-venous and intraocular pressure. Preliminary report of animal studies," Investigative Ophthalmology, vol. 5(1), pp. 59-64, Feb. 1966.

Mapea et al., "The pressures in the episcleral veins, Schlemm's canal and the trabecular meshwork in monkeys: Effects of changes in intraocular pressure," Exp. Eye Res, vol. 49 pp. 645-663, Oct. 1989.

Nicolle et al., "A silastic ndon prosthesis as an adjunct to flexor tendon grafting . . . ," British Journal of Plastic Surgery, vol. 22(3-4), pp. 224-236 (year of pub. sufficiently earlier than effective US filing date and any foreign priority date) 1969.

Rubin et al., "The use of acellular biologic tissue patches in foot and ankle surgery," Clinics in Podiatric Medicine and Surgery, vol. 22, pp. 533-552, Oct. 2005.

Schultz, "Canaloplasty procedure shows promise for open-angle glaucoma in European study," Ocular Surgery News, pp. 34-35, Mar. 1, 2007.

Spiegel et al., "Schlemm's canal implant: A new method to lower intraocular pressure in patients with POAG," Ophthalmic Surgery and Lasers, vol. 30(6), pp. 492-494, Jun. 1999.

Stetson et al., "Arthroscopic treatment of partial rotator cuff tears," Operative Techniques in Sports Medicine, vol. 12(2), pp. 135-148, Apr. 2004.

Valdez et al., "Repair of digital flexor tendon lacerations in the horse using carbon fiber implants," JAYMA, vol. 177(5), pp. 427-435, Sep. 1, 1980.

Wikipedia, the free encyclopedia, Rotator cuff tear, downloaded from <http://en.wikipedia.org/wiki/Rotator_cuff_tear> 14 pages, on Dec. 6, 2012.

Alexander et al., "Ligament and tendon repair with an absorbable polymer-coated carbon fiber stent," Bulletin of the Hospital for Joint Diseases Orthopaedic Institute, vol. 46(2), pp. 155-173, Fall 1986.

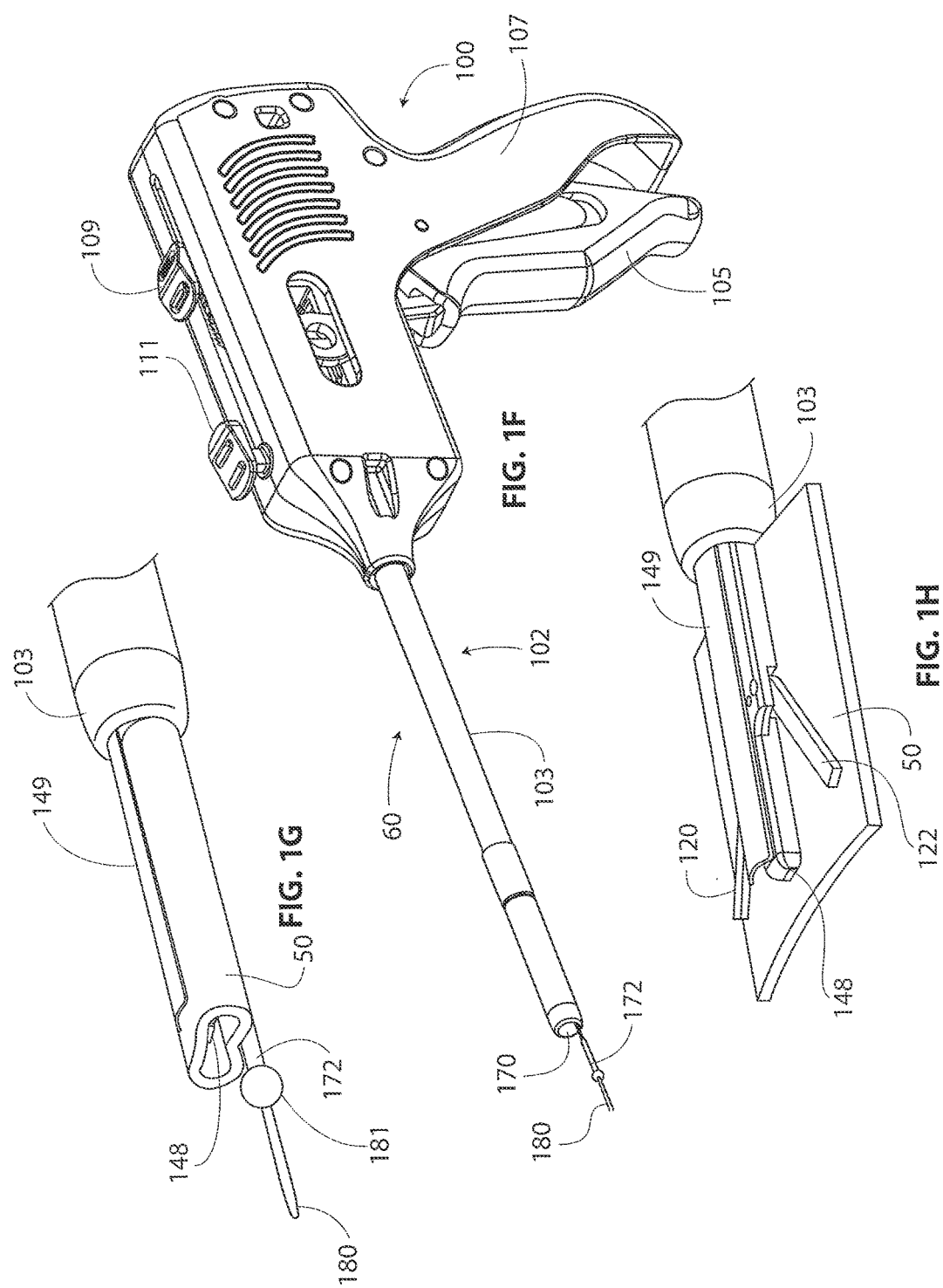

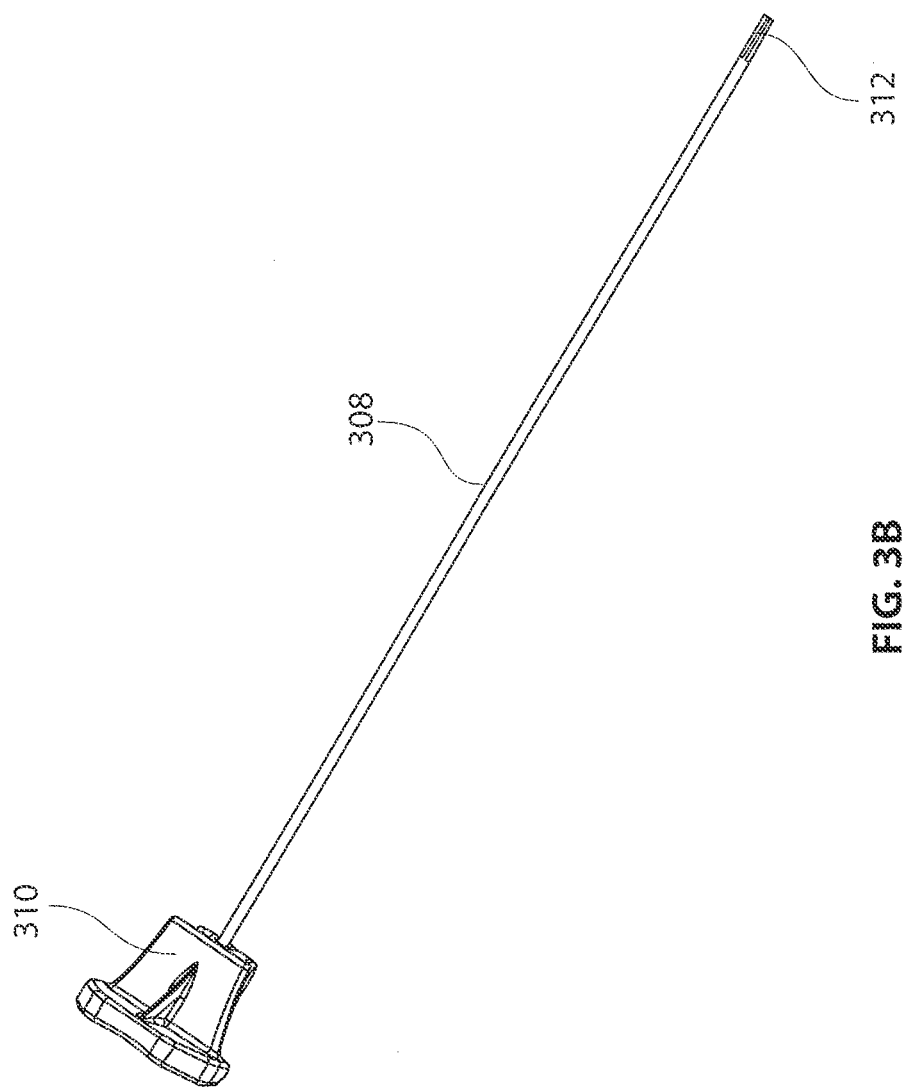

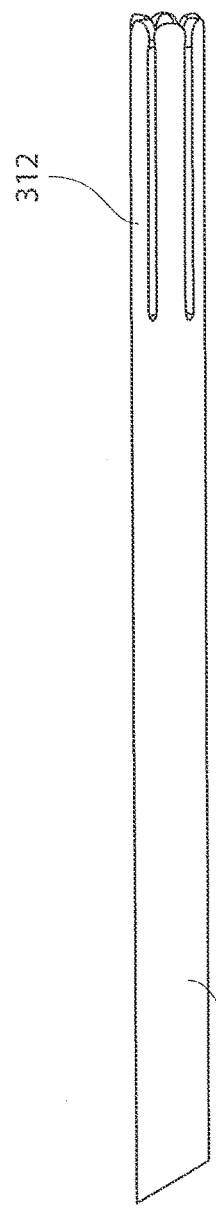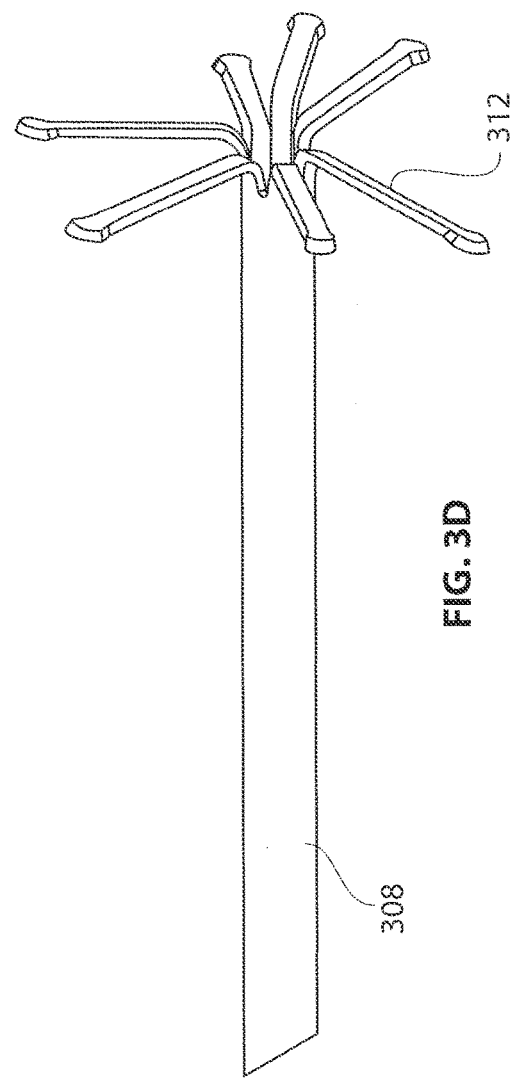
FIG. 3C
FIG. 3D

METHODS AND APPARATUS FOR DELIVERING AND POSITIONING SHEET-LIKE MATERIALS IN SURGERY

CROSS REFERENCE TO RELATED APPLICATIONS

This application is a continuation of U.S. application Ser. No. 13/889,757, filed May 8, 2013, which is a continuation of U.S. application Ser. No. 13/722,796, filed Dec. 20, 2012, which claims the benefit of U.S. Provisional Patent Application Ser. No. 61/581,628 filed on Dec. 29, 2011, the disclosures of each incorporated herein by reference.

The present disclosure is related to the following commonly assigned co-pending applications, the disclosures of which are incorporated herein by reference: U.S. Provisional Application No. 61/443,169 filed on Feb. 15, 2011; U.S. Provisional Application No. 61/581,629 filed on Dec. 29, 2011; and U.S. Provisional Application No. 61/581,631 filed on Dec. 29, 2011.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates generally to orthopedic medicine and surgery. More particularly, the present invention relates to methods and apparatus for forming pilot holes in bone for inserting fasteners and fixation of sheet-like materials, such as for treating tendons or like tissue of articulating joints, such as tendons in the rotator cuff of the shoulder.

BACKGROUND

The glenohumeral joint of the shoulder is found where the head of the humerus mates with a shallow depression in the scapula. This shallow depression is known as the glenoid fossa. Six muscles extend between the humerus and scapula and actuate the glenohumeral joint. These six muscles include the deltoid, the teres major, and the four rotator cuff muscles. The rotator cuff muscles are a complex of muscles. The muscles of the rotator cuff include the supraspinatus, the infraspinatus, the subscapularis, and the teres minor. The centering and stabilizing roles played by the rotator cuff muscles are critical to the proper function of the shoulder. The rotator cuff muscles provide a wide variety of moments to rotate the humerus and to oppose unwanted components of the deltoid and pectoral muscle forces.

The muscles of the rotator cuff arise from the scapula. The distal tendons of the rotator cuff muscles splay out and interdigitate to form a common continuous insertion on the humerus. The supraspinatus muscle arises from the supraspinatus fossa of the posterior scapula, passes beneath the acromion and the acromioclavicular joint, and attaches to the superior aspect of the greater tuberosity. The mechanics of the rotator cuff muscles are complex. The rotator cuff muscles rotate the humerus with respect to the scapula, compress the humeral head into the glenoid fossa providing a critical stabilizing mechanism to the shoulder (known as concavity compression), and provide muscular balance. The supraspinatus and deltoid muscles are equally responsible for producing torque about the shoulder joint in the functional planes of motion.

The rotator cuff muscles are critical elements of this shoulder muscle balance equation. The human shoulder has no fixed axis. In a specified position, activation of a muscle creates a unique set of rotational moments. For example, the anterior deltoid can exert moments in forward elevation, internal rotation, and cross-body movement. If forward elevation is to occur without rotation, the cross-body and internal rotation moments of this muscle must be neutralized by other muscles, such as the posterior deltoid and infraspinatus. The timing and magnitude of these balancing muscle effects must be precisely coordinated to avoid unwanted directions of humeral motion. Thus the simplified view of muscles as isolated motors, or as members of force couples must give way to an understanding that all shoulder muscles function together in a precisely coordinated way—opposing muscles canceling out undesired elements leaving only the net torque necessary to produce the desired action. Injury to any of these soft tissues can greatly inhibit ranges and types of motion of the arm.

With its complexity, range of motion and extensive use, a common soft tissue injury is damage to the rotator cuff or rotator cuff tendons. Damage to the rotator cuff is a potentially serious medical condition that may occur during hyperextension, from an acute traumatic tear or from overuse of the joint. With its critical role in abduction, rotational strength and torque production, the most common injury associated with the rotator cuff region is a strain or tear involving the supraspinatus tendon. A tear at the insertion site of the tendon with the humerus, may result in the detachment of the tendon from the bone. This detachment may be partial or full, depending upon the severity of the injury or damage. Additionally, the strain or tear can occur within the tendon itself. Injuries to the supraspinatus tendon and current modalities for treatment are defined by the type and degree of tear. The first type of tear is a full thickness tear, which as the term indicates, is a tear that extends through the thickness of the supraspinatus tendon regardless of whether it is completely torn laterally. The second type of tear is a partial thickness tear which is further classified based on how much of the thickness is torn, whether it is greater or less than about 50% of the thickness.

The accepted treatment for a full thickness tear or a partial thickness tear greater than 50% includes reconnecting the torn tendon via sutures. For the partial thickness tears greater than 50%, the tear is completed to a full thickness tear by cutting the tendon prior to reconnection. In some procedures, the surgeon will position a sheet-like patch over the sutured area to strengthen the repair and try to prevent the sutures from tearing through the tendon. The placement of the patch can be accomplished readily in an open surgical procedure, however, placement and attachment of the patch in an arthroscopic procedure has been shown to be very difficult.

In contrast to the treatment of a full thickness tear or a partial thickness tear of greater than 50%, the current standard treatment for a partial thickness tear less than 50% usually involves physical cessation from use of the tendon, i.e., rest. Specific exercises can also be prescribed to strengthen and loosen the shoulder area. In many instances, the shoulder does not heal, and the partial thickness tear can be the source of chronic pain and stiffness. Further, the pain and stiffness may cause restricted use of the limb which tends to result in further degeneration or atrophy in the shoulder. Surgical intervention may be required for a partial thickness tear of less than 50%, however, current treatment interventions do not include repair of the tendon, and rather the surgical procedure is directed to arthroscopic removal of bone to relieve points of impingement or create a larger tunnel between the tendon and bone that is believed to be causing tendon damage. As part of the treatment, degenerated tendon may also be removed using a debridement procedure in which tendon material is removed or ablated. Again, the tendon partial thickness tear is not repaired. Several authors have reported satisfactory early post-operative results from these procedures, but over time recurrent symptoms have been noted. In the event of recurrent symptoms, many times a patient will "live with the pain". This may result in less use of the arm and shoulder which causes further degeneration of the tendon and may lead to more extensive damage. A tendon repair would then need to be done in a later procedure if the prescribed treatment for the partial tear was unsuccessful in relieving pain and stiffness or over time the tear propagated through injury or degeneration to a full thickness tear or a partial thickness tear greater than 50% with attendant pain and debilitation. A subsequent later procedure would include the more drastic procedure of completing the tear to full thickness and suturing the ends of the tendon back together. This procedure requires extensive rehabilitation, has relatively high failure rates and subjects the patient who first presented and was treated with a partial thickness tear less than 50% to a second surgical procedure.

As described above, adequate devices and methods for positioning sheet-like patches or implants during an arthroscopic procedure do not currently exist. It has been shown to be very difficult to properly position and attach a sheet-like implant unless the treatment site is accessed in an open procedure. Further, adequate procedures do not exist for repairing a partial thickness tear of less than 50% in the supraspinatus tendon. Current procedures attempt to alleviate impingement or make room for movement of the tendon to prevent further damage and relieve discomfort but do not repair or strengthen the tendon. Use of the still damaged tendon can lead to further damage or injury. Prior damage may result in degeneration that requires a second more drastic procedure to repair the tendon. Further, if the prior procedure was only partially successful in relieving pain and discomfort, a response may be to use the shoulder less which leads to degeneration and increased likelihood of further injury along with the need for more drastic surgery. Therefore, it would be beneficial to be able to position, deliver and attach a sheet-like implant to a treatment site in an arthroscopic procedure. It would also be beneficial to treat partial thickness tears greater than 50% without cutting the untorn portion of the tendon to complete the tear before suturing back together. There is a large need for surgical techniques and systems to position, deploy and attach implants during an arthroscopic procedure and to treat partial thickness tears and prevent future tendon damage by strengthening or repairing the native tendon having the partial thickness tear.

SUMMARY OF THE DISCLOSURE

The disclosure is directed to an implant delivery system for accurately positioning and deploying or delivering a sheet-like implant. One embodiment provides an implant delivery system including an implant retainer assembly and an implant spreader assembly. The implant retainer assembly and the implant spreader assembly are provided proximate the distal end of a delivery shaft. The implant retainer assembly is configured to releasably couple a sheet-like implant thereto for positioning the sheet-like implant at a treatment site. The implant spreader assembly is configured to expand the sheet-like implant so that the sheet-like implant covers the treatment site.

The implant delivery system can include a distal guidewire port located proximate the distal end of the delivery system a fixed and known distance both laterally and longitudinally relative to an implant when it is loaded onto the implant retainer assembly. With this embodiment, the implant delivery system can be included in a kit that includes a guidewire or be used in conjunction with a guidewire that is provided separately from the implant delivery system. The guidewire can include a proximally extending length of wire that extends from a distal tissue retention member. The tissue retention member provides a temporary connection of the distal end of the guidewire to the bone or other tissue. The tissue retention member includes means for temporarily or reversibly fixing the distal end of the guidewire to tissue, such as bone. The means for affixing can include a K-wire (Kirshner wire) which can be a smooth stainless steel pin with a drill tip that cuts into bone when rotated. Alternatively, the means for fixing can include a screw that is threaded or a fine pin that is hammered into bone or other tissue. The fine pin can include barbs or other projections and/or surface texture that aid in temporarily fixing the distal end of the guidewire to the bone or other tissue. The proximally extending wire can be coupled to the tissue retention member via a strain relief that allows the wire to bend proximate the tissue retention member. The strain relief can include a spring or a coil.

The positional relationship (lateral and longitudinal) of a loaded implant relative to the distal guidewire port is advantageously used to position the implant delivery system relative to a first fixed point on the anatomy of the patient and assures the deployed implant will properly cover the treatment site. The first fixed point on the anatomy can be used as the location of the distal end of the guidewire as fixed to the bone or other tissue. The proximal end of the guidewire is fed through the distal guidewire port, and the delivery system is guided by the wire to abut the anatomy or the tissue retention member proximate the fixed point.

In one method of using the present system, a first fixed point is determined through observation and/or measurement of a treatment site or tissue to be covered by the implant relative to other anatomy. For example, in treating a rotator cuff injury, the surgeon can measure the supraspinatus tendon lateral width and observe the location of the line generally defining the point of insertion of the tendon into the humeral head. With these measurements known, along with the known size of implant to be used and the longitudinal/lateral location of the loaded implant relative to the guidewire port, a best location for the first fixed point can be selected and the guidewire fixed thereto.

Determining a first fixed point for the implant location, however, may not adequately position the implant as it can be rotated, at least to some degree, about that first fixed point. Therefore, in some embodiments, at least a second anatomical point or position is identified and/or marked to assure the implant is rotated to proper position on the first fixed point. In some embodiments a third anatomical point or position may also be identified and/or marked, in which embodiment the second and third point can define a line which is generally parallel to an edge of the implant when properly rotated about the first point. In treating the supraspinatus tendon, a marker can be placed through the skin and tendon while viewing the articular side of the supraspinatus tendon where the biceps tendon is also visible. The marker can be inserted adjacent the biceps tendon to delineate its location and assure the implant is rotated to generally parallel the biceps tendon and avoid any staples attaching to such tendon which may interfere with its function.

In some exemplary embodiments, the implant spreader assembly includes a first arm and a second arm each having a proximal and a distal end. The proximal end of each arm is pivotably connected proximate the distal end of the delivery shaft. The first and second arms are moveable between a closed position and an open position. When the first and second arms are in the closed position, the arms extend generally in the longitudinal direction. When pivoting to the open position the distal end of each arm travels in a generally transverse direction to spread an implant that has been positioned on the implant retainer assembly. When pivoting from the open position to the closed position, the first arm and the second arm may travel in different planes.

In some exemplary embodiments, a sheath is disposed about the implant spreader assembly. The sheath is slidable in a direction generally parallel to a longitudinal axis of the delivery shaft such that the sheath can be retracted proximally from around the implant spreader assembly. The sheath can include a bullet nose distal end to ease insertion into the shoulder space.

A sheet-like implant may be releasably coupled to the implant retainer assembly. When this is the case, the sheet-like implant may fit within the sheath when the implant spreader is in the closed position. The sheet-like implant may then be expanded to cover a treatment site when the sheath is retracted and the implant spreader is opened. In some useful embodiments, the sheet-like implant extends tautly between the arms of the implant spreader when the arms are in the open position. The sheet-like implant may assume a rolled configuration when the implant expander is in the closed position.

In some exemplary embodiments, the first arm and the second arm pivot transversely in different planes such that in the open position the sheet-like implant extending between the arms forms a generally curved surface to conform to a generally curved treatment site when placed thereon. In some instances, the first arm and the second arm pivot transversely in the same plane such that in the open position the sheet-like implant extending between the arms forms a generally flat surface.

In some embodiments, the implant retainer assembly comprises a center post disposed proximate the distal end of the delivery shaft. A mating surface having a longitudinally extending groove generally parallel and spaced from the center post cooperates with the center post to retain the implant when it is slidably disposed therebetween. The center post and mating surface define a slot that is dimensioned to receive the sheet-like implant.

Another embodiment provides an implant delivery system including a delivery shaft having a proximal end and a distal end defining a generally longitudinal direction. An implant spreader assembly is provided proximate the distal end of the delivery shaft. A sheet-like implant is coupled to the implant spreader such that the implant is folded when the arms of the implant spreader are in a closed position and unfolded when the arms of the implant spreader are in an open position. The implant spreader assembly may be used to unfold the sheet-like implant, for example, to spread the implant over a treatment site within the body. A hood that extends distally from the distal end of the shaft, generally parallel to the implant spreader assembly can be included. The hood is spaced radially from the implant retention assembly and retains the implant in folded configuration when unsheathed until deployment of the implant spreader.

A method of treating a site such as a rotator cuff of a shoulder may include the step of providing an implant delivery system as described above. The treatment site or shoulder of the patient may be inflated to create a cavity therein. The treatment site can be observed and/or measured using a probe or other instrument to identify the proper implant size and a first anatomical location for affixing the distal end of a guidewire such that abutment of the guidewire port proximate this location will place the implant at a desired location when deployed. A guide wire is affixed to the anatomical location selected, as for example, a point near the insertion of the supraspinatus tendon on the humeral head. Further, a second and/or third anatomical point can be identified that will give proper rotational position to the implant delivery system. These points can be identified and markers placed to provide a visual reference. The implant delivery system can be tracked over the guidewire to abut the first reference point. The implant and the implant spreader assembly may be unsheathed inside the cavity. The implant may be spread over a target tissue at the treatment site and rotated to align with the second and/or third reference points as marked. The implant may be affixed to the target tissue. The implant may be released from the implant delivery system. The implant spreader assembly may be removed from the cavity. In some cases, the implant spreader assembly is assuming the closed configuration while the implant spreader assembly is withdrawn from the cavity.

BRIEF DESCRIPTION OF THE DRAWINGS

FIG. 1F is a perspective view of an implant delivery system having a guidewire extending from a distal guidewire port;

FIG. 1G is a partial perspective view illustrating the distal portion of the implant delivery system of FIG. 1F, including an implant folded and mounted on the implant retainer assembly and a guidewire extending from the guidewire port;

FIG. 1H is partial perspective view illustrating the distal portion of the implant delivery system of FIG. 1F after activation of the implant spreader assembly to unfurl the implant;

FIG. 3B is a perspective view of the marker of FIG. 3A as removed from the needle-like sheath;

FIG. 3C is a partial perspective view of the distal portion of the marker of FIG. 3B illustrating a plurality of distal arms extending longitudinally as they would be when constrained within the sheath;

FIG. 3D is a partial perspective view of the arms of FIG. 3C as deployed upon removal of the sheath to extend laterally and retain the marker in tissue;

DETAILED DESCRIPTION

The following detailed description should be read with reference to the drawings in which similar elements in different drawings are numbered the same. The drawings, which are not necessarily to scale, depict illustrative embodiments and are not intended to limit the scope of the invention.

The present disclosure is directed to an implant delivery system that is particularly useful for accurately positioning and deploying or delivering a sheet-like implant to a treatment Site. The delivery system is discussed in detail with respect to treatment of tendons in articulating joints, specifically the supraspinatus tendon of the rotator cuff in the shoulder. However, it is recognized that the delivery system and other components of a kit disclosed herein can be utilized in any areas of the body wherein it is desired to accurately position a sheet-like implant, especially during an arthroscopic procedure where access and visibility are limited.

The implant delivery system can be used in conjunction with a guidewire or be part of a kit that includes a guidewire. The guidewire is configured with a distal end that attaches to bone or other tissue at a first fixed point that is determined through observation and measurement of the treatment site. The first fixed point is determined based on knowledge of the size of the implant to be used, the known location of a distal guidewire port on the delivery system relative to an implant when it is loaded on the delivery system and the measured/observed anatomy of the treatment site. Once the guidewire is attached at the first fixed point, the delivery system can track over the wire to the proper position for delivering the implant. Details of the guidewire design are disclosed with respect to the discussion of FIG. 2A-2E. The above method, as applied to treatment of the supraspinatus tendon of the rotator cuff is described in detail with respect to FIGS. 8A-8N.

The delivery system of this disclosure can also be used in conjunction with other tissue position markers or included in a kit with tissue position markers. Identifying a first fixed point for attachment of the guidewire may not be sufficient in some applications to accurately position the implant as the delivery system can be rotated to some degree about the first point. By using visual observation and/or other measurement techniques a second, and if necessary a third, fixed point can be identified and marked with the markers to be used as a reference point or line for proper rotation or orientation of the implant as positioned over the wire. The markers are described in detail with respect to FIGS. 3A-3D and the method of marking a second and third fixed point are described for the rotator cuff with respect to FIGS. 8A-8N.

Figure 1A:
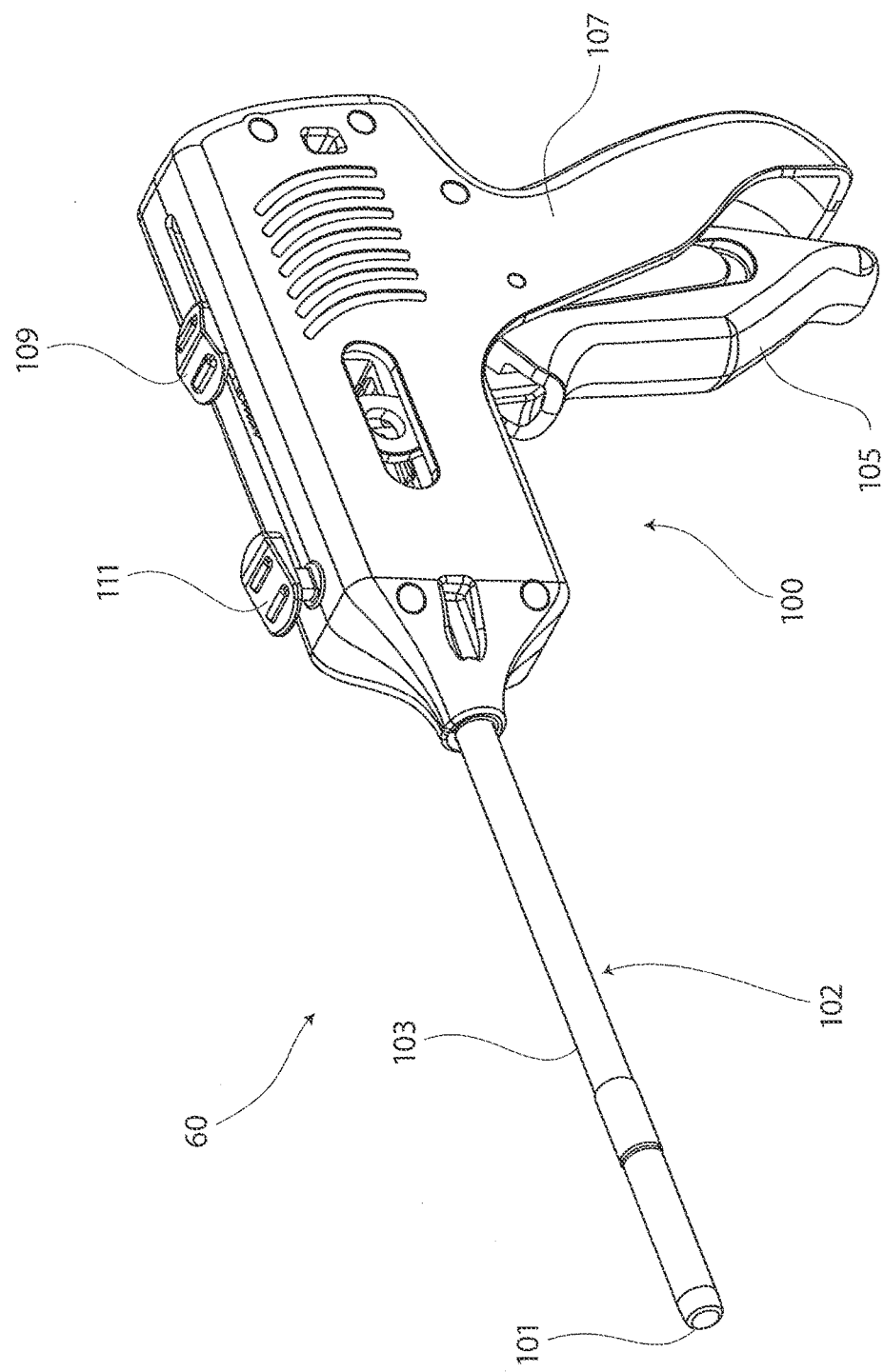
FIG. 1A is a perspective view illustrating an exemplary implant delivery system including an actuating handle assembly and a barrel.

Referring now to FIG. 1A, a perspective view of an exemplary implant delivery system 60 is shown. Implant delivery system 60 includes a handle assembly 100 and barrel assembly 102. As depicted in FIG. 1A, the outer barrel assembly 102 is a sheath 103 attached to and extending distally from the handle assembly 100. The sheath 103 can include a bullet nose or tapered distal tip to aid in inserting the delivery system 60 through an incision to the treatment site. The sheath 103 covers a delivery assembly as discussed with respect to FIG. 1B below. The sheath 103 of implant delivery system 60 is coupled to the handle assembly 100 in a fixed position, in the embodiment depicted. In alternative embodiments the sheath 103 may be reciprocally engaged by the handle assembly 100 to allow longitudinal movement in response to movement of the trigger 105. The sheath can be opaque, transparent or anywhere between. In some embodiments, at least a distal portion of the sheath is transparent so that an implant loaded within the sheath can be inspected for condition and observed as to how the implant is folded within the lumen.

Figure 1B:
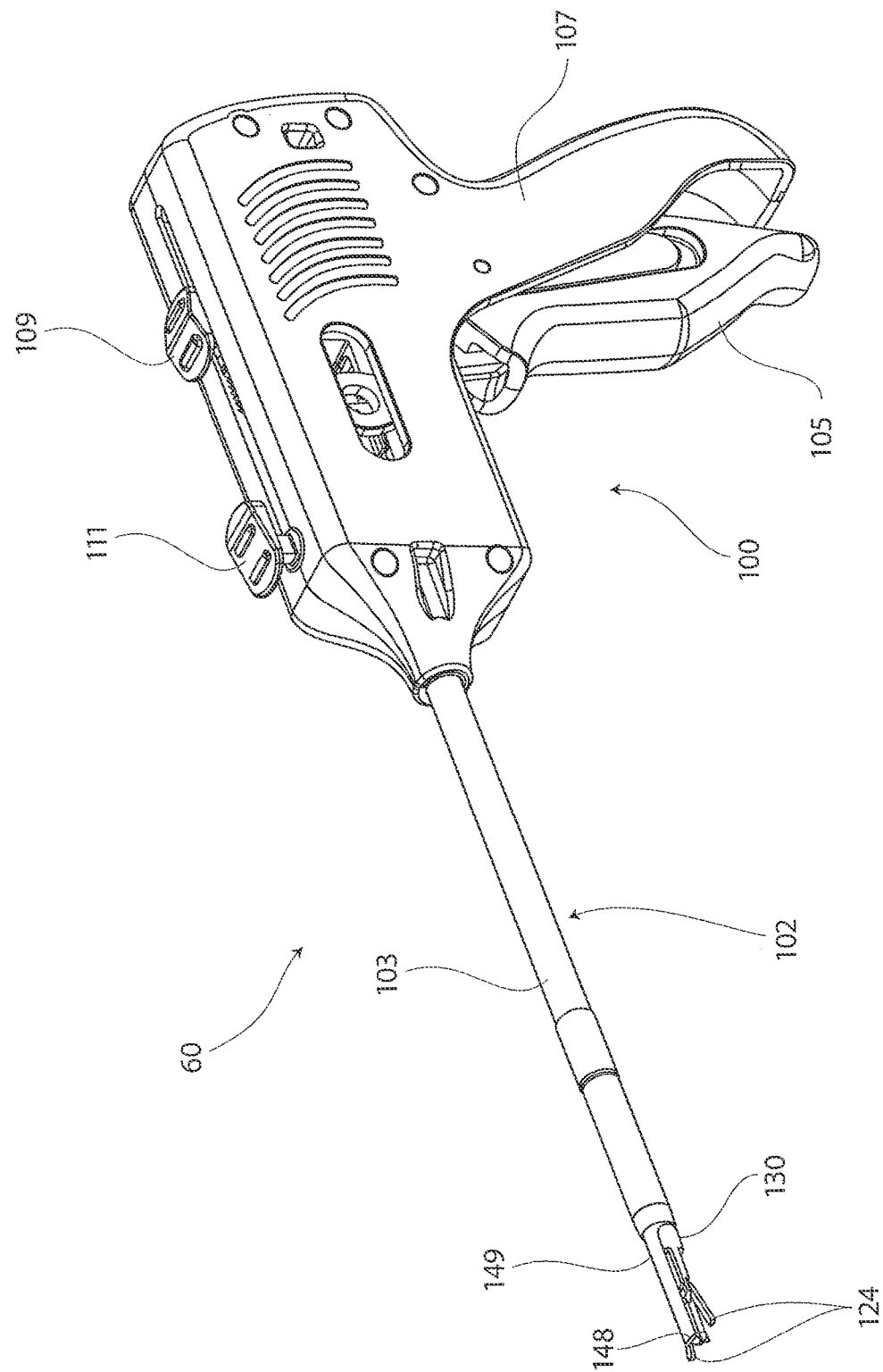
FIG. 1B is a an alternative perspective view of the implant delivery system of FIG. 1A illustrating an implant retainer assembly and implant spreader assembly on a distal portion of the delivery system extending beyond the sheath.

As depicted in FIG. 1B, the handle assembly 100 includes a body 107 and reciprocating trigger 105 attached thereto. The handle assembly also includes a first button 111 that releasably engages a delivery shaft 130 (discussed below with respect to FIG. 1D). The first button 111 allows movement of the delivery shaft 130 to extend beyond the sheath 103 for loading an implant and reverse movement pulls the delivery shaft 130 back into the sheath 103.

A second button 109 is connected to longitudinal members that extend within the sheath to move arms of an implant spreader assembly 124 (see FIG. 1B). Pushing of the button releases engagement with the longitudinal members and allows the arms to close as the overall system is pulled from the implant site.

Figure 1C:
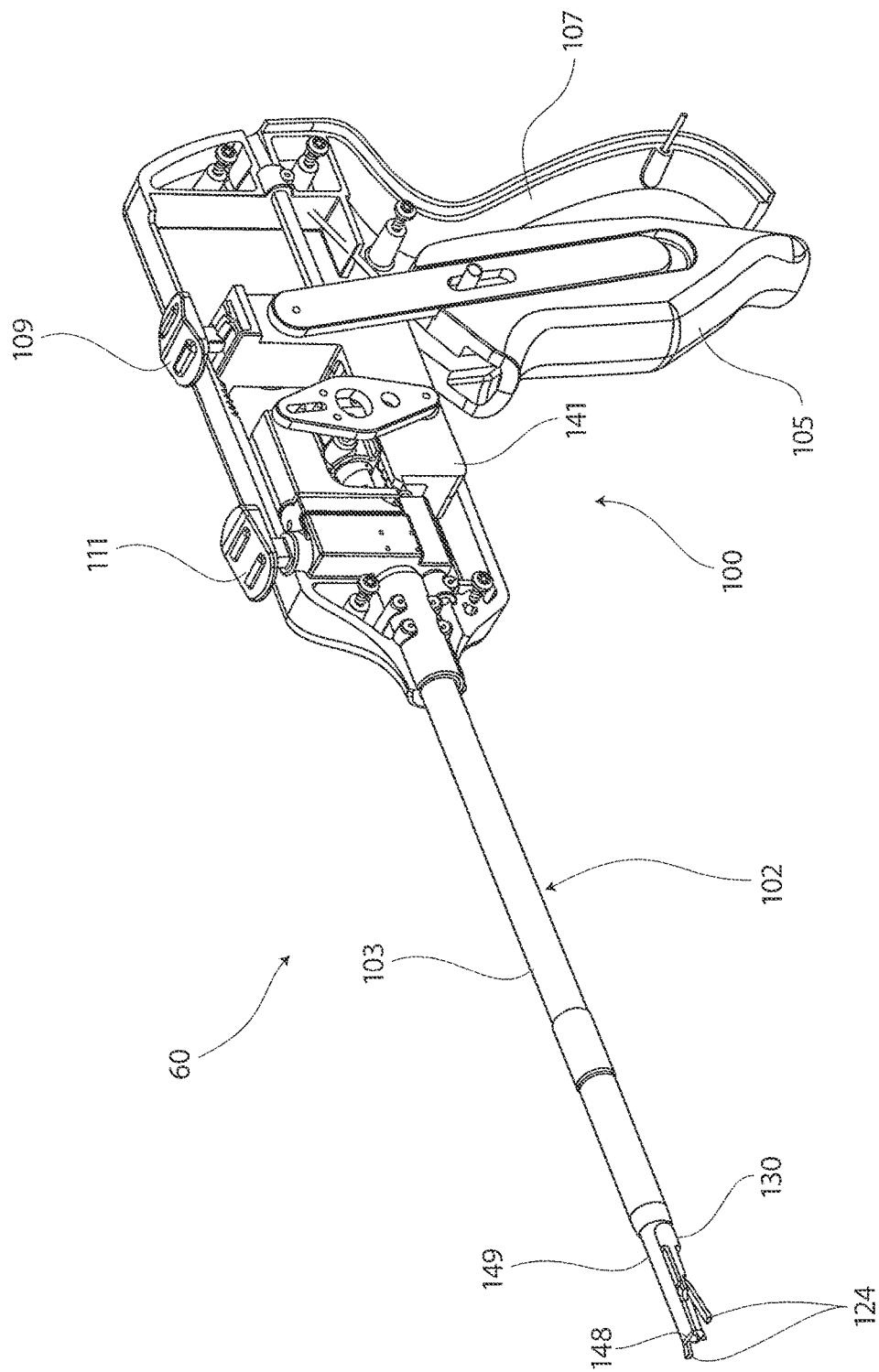
FIG. 1C is a partial cross sectional view of the implant delivery assembly of FIG. 1A depicting the actuating mechanism in the handle assembly.

FIG. 1B depicts the implant delivery system 60 of FIG. 1A with a delivery shaft 130 extended distally beyond the sheath 103 as would be done during delivery of an implant. The extended delivery shaft 130 also allows visualization of the working components on the distal end of the delivery system. These include an implant retainer assembly 148, an implant spreader assembly 124 and a hood 149. To better visualize the extension of the delivery shaft 130 relative to the handle assembly 100. FIG. 1C depicts the delivery system of FIG. 1B with a portion of the body 107 removed to expose the linkages between the trigger 105, first button 111 and second button 109 with the barrel assembly 102. As illustrated, in this representative embodiment, the sheath 103 is rigidly fixed to a distal portion of the handle 100 with the delivery shaft 130 slidably disposed therein. The delivery shaft is linked to a first member 141 which is also linked to both the trigger 105 and first push button 111. Distal movement of the first push member 141, whether by movement of the trigger 105 or the push button 109 being moved distally causes distal extension of the delivery shaft 130 relative to the sheath 103.

Figure 1D:
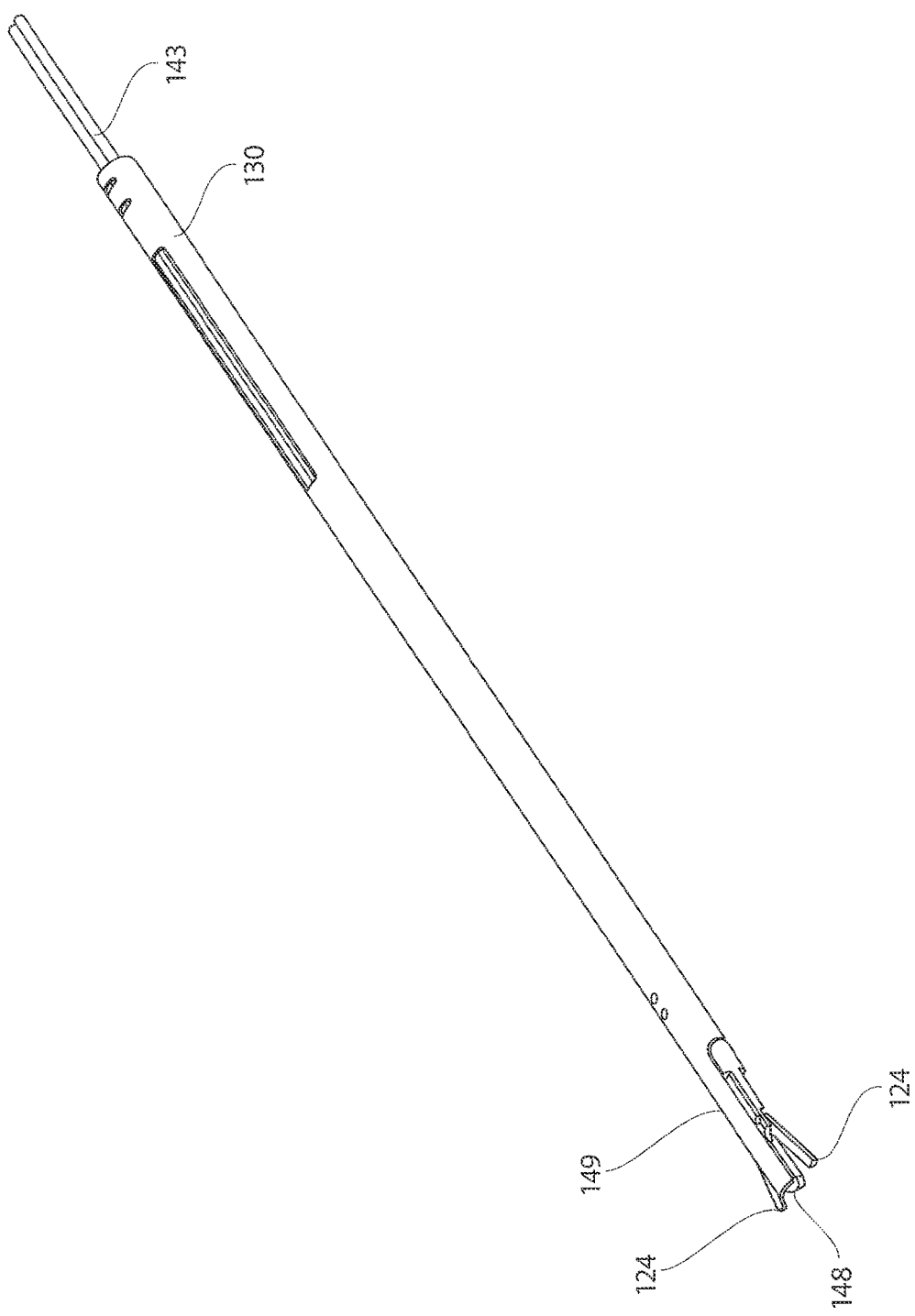
FIG. 1D is a perspective view of the delivery shaft including the implant spreader and implant retainer assemblies of FIG. 1B as removed from the sheath and handle.

With reference to FIG. 1D, the delivery shaft 130 is depicted in more detail as removed from the sheath 103 and disconnected from the handle assembly 100. The delivery shaft 130 includes a pair of longitudinally extending members 143 that are operably connected to the tissue spreader assembly 124. Linkage (not shown) within the handle assembly 100 connects the proximal portion of the longitudinally extending members 143 such that pulling on the trigger after the delivery shaft 130 has been extended causes distal movement of the longitudinally extending members 143 to operate the spreader assembly 124. One of skill in the art will recognize that the mechanisms described are representative of one working embodiment of a handle coupled to the barrel assembly 102 and that other actions and linkages can be used to operate the working portions of the implant delivery system 60, to include both extension of the delivery shaft or retraction of the sheath and also deployment of the spreader assembly.

Figure 1E:
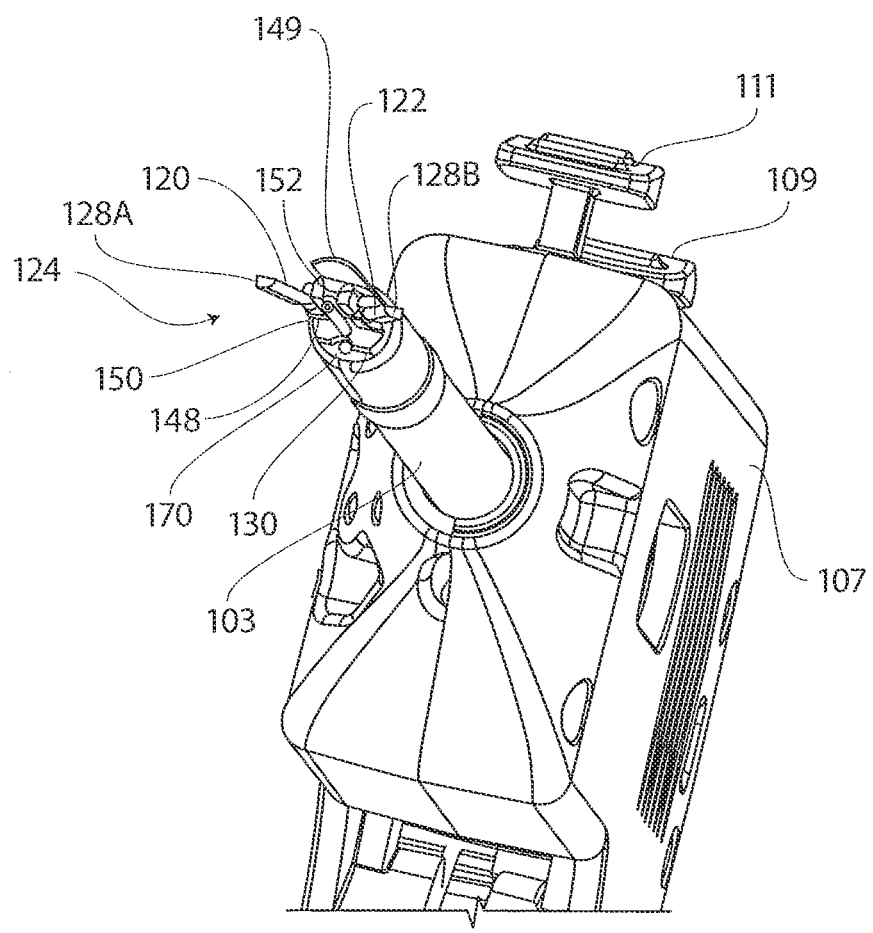
FIG. 1E is an alternative perspective view of the implant delivery system of FIG. 1A illustrating details of the implant retainer assembly and the location of a distal guidewire port.

As best seen in FIG. 1E, a first arm 120 and a second arm 122 can be seen extending distally from the delivery shaft 130. First arm 120 and second arm 122 are both part of an implant spreader assembly 124. Implant spreader assembly 124 may be used to carry a sheet-like implant to a location within the human body. Implant spreader assembly 124 may also be used to unfold the sheet-like implant so that the sheet-like implant covers a treatment site within the body.

In the exemplary embodiment of FIG. 1E, first arm 120 and second arm 122 are disposed in an open position. First arm 120 and second arm 122 are capable of moving between the open position where the arms extend laterally and a closed position wherein the arms generally extend longitudinally parallel to the delivery shaft 130. When pivoting to the open position the arms rotate so that distal end 128A of first arm 120 and distal end 128B of second arm 122 move away from each other in generally transverse or lateral directions. In some embodiments the distal ends of the arms lie in the same plane as the sheath in both the open and closed positions, however, in other embodiments disclosed herein, the arms may move in different planes relative to each other so that the implant will take a curved shape in the open position to better conform to the treatment site as laterally delivered. Further, in some alternative embodiments, one arm may be stationary while the other rotates to spread the implant.

As also shown in greater detail in FIG. 1E, the implant delivery system 60 also includes an implant retainer assembly 148 located near a distal end of delivery shaft 130. In the exemplary embodiment of FIG. 1E, implant retainer assembly 148 comprises a center post 150 post disposed proximate the distal end of the delivery shaft 130 that cooperates with a mating surface 152 having a longitudinally extending groove 154 generally parallel and spaced from the center post wherein the mating surface and center post foi in a slot therebetween to retain the implant when it is slidably disposed thereon.

As also indicated on FIG. 1E, the implant delivery system includes a guidewire port 170 located proximate the distal end of the delivery shaft 130. The guidewire port 170 is sized for receiving a proximal end of a guidewire, discussed below with respect to FIGS. 2A-2E, therethrough. The guidewire port location is positioned in known relation to an implant on the implant retainer assembly so that tracking the implant delivery system over the guidewire to a known guidewire location fixes the location to which the implant will be delivered relative thereto.

FIG. 1F depicts the implant delivery system of FIG. 1A with a guidewire 172 having been fed from a proximal end thereof through the guidewire port 170 and extending distally from the end of the barrel 102. The interior of the delivery shaft provides a lumen for receiving the proximal portion of the guidewire as it is fed through the guidewire port 170. As depicted, the guidewire 172 includes a tissue retention member 180 on the distal end thereof. In use, the tissue retention member 180 is affixed to bone or other tissue at a desired anatomical location. The implant delivery system 60 is then tracked over the guidewire from its proximal end until the distal end of the implant delivery system (after the delivery shaft is extended from the sheath) or delivery shaft abuts the tissue or guidewire proximate the point at which the guidewire is fixed to the bone or other tissue.

The relationship between the implant delivery system 60, the guidewire 172 and a sheet-like implant 50 mounted thereon for delivery can be better understood, in an exemplary embodiment, by reference to FIG. 1G. FIG. 1G depicts a distal portion of the delivery system with the delivery shaft extended beyond the sheath. A sheet-like implant 50 is held in place by the implant retention member 148 as previously described. Further, the implant 50 is shown in a folded configuration as it would fit in the sheath and remains in this configuration when the delivery shaft is extended because a hood 149 is included in this embodiment for receiving the edges of the implant 50 thereunder. The guidewire 172 is depicted extending distal of the implant. In use, the delivery shaft would be fed further distal over the guidewire until the ball 181 is in contact or nearly in contact with the guidewire port at the distal end of the delivery shaft, which is generally about 5 mm. distal of the proximal end of the implant or in alternative embodiments may be in longitudinal alignment with the proximal end of the implant. The guidewire port is also generally in lateral alignment with the center of the implant. Thus, the location of the attachment of the guidewire will generally conform to a location 5 mm. distal of the proximal end of the implant and at the lateral center of the implant when delivered in this embodiment. Other spacing could be used if desired, with the longitudinal and lateral relationship of the implant relative to the guidewire port being known.

FIG. 1H depicts the distal portion of the implant delivery system illustrated in FIG. 1G after the implant spreader assembly 124 is deployed. As shown, the lateral movement of the arms 120, 122 pull the edge of the implant out from under the hood 149 and cause the implant 50 to lay flat. The implant retention member 148 continues to hold the implant on the assembly in order to allow movement of the implant to a desired position.

Figure 2A:
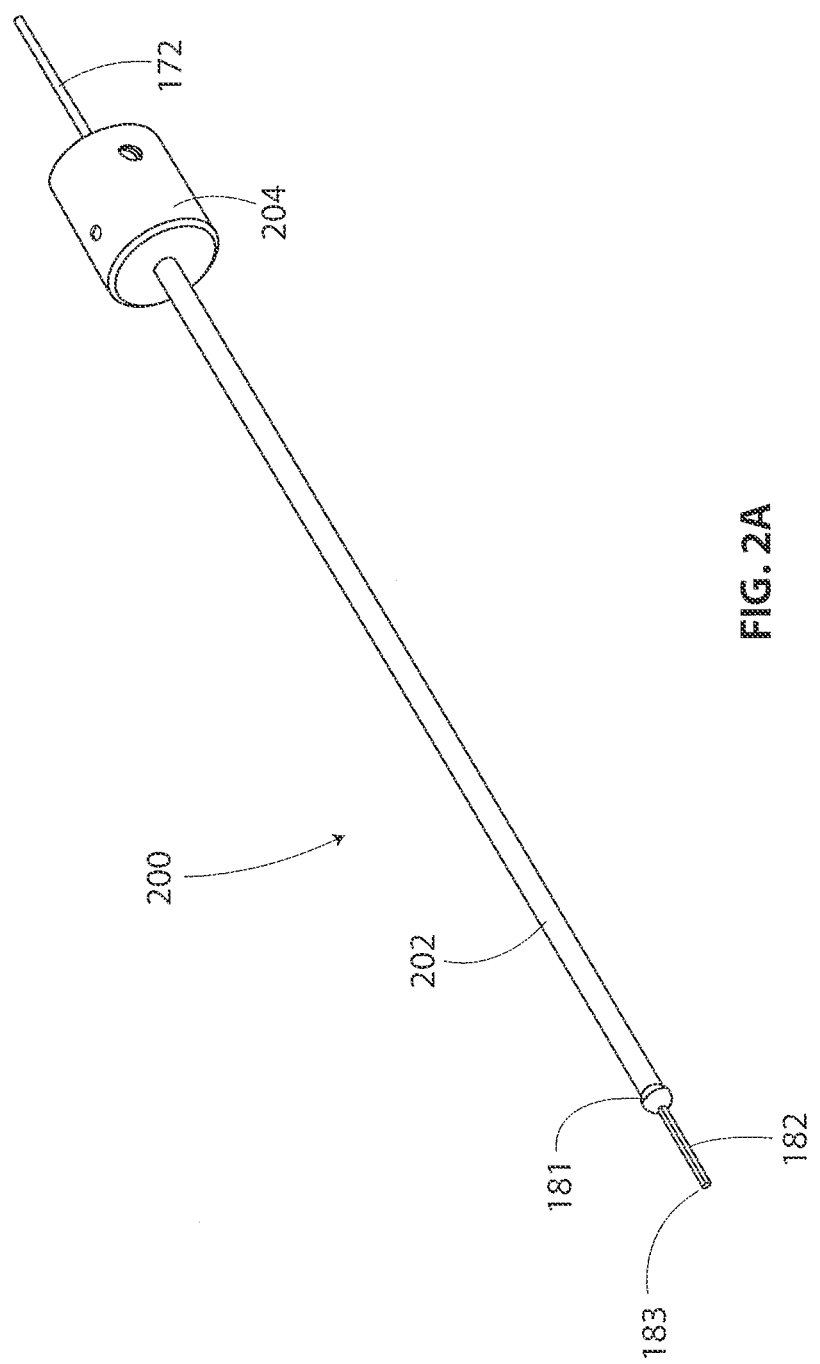
FIG. 2A is a perspective view of a guidewire as disposed in a delivery assembly for attachment to bone or other tissue.

Referring now to FIG. 2A, a representative guidewire 172 and delivery system 200 is illustrated. The delivery system can include a shaft 202 having a lumen 203 extending therethrough. The proximal end of the shaft includes means for holding and directing the shaft 204 and the proximal end of the shaft can be attached to a rotating tool (not shown). The guidewire 172 extends through the shaft lumen. The shaft further includes mean for rotational engagement between the delivery system and the guidewire. When inserted in the lumen, the guidewire rotates as the shaft rotates. Means for rotational engagement between the shaft and guidewire are generally known, as for example, a keyed portion near the distal end of the guidewire may engage a mating surface extending from the shaft.

Figure 2B:
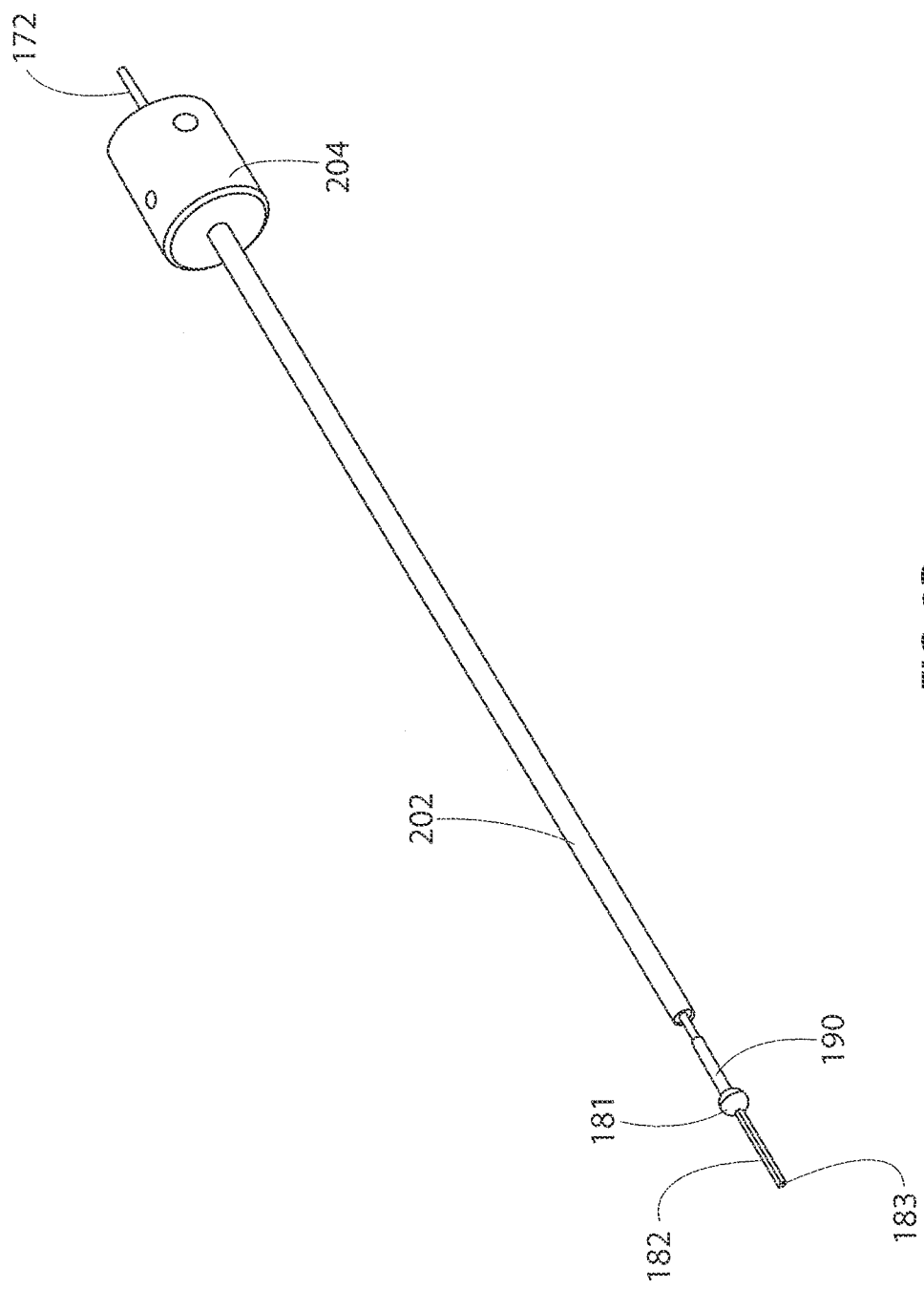
FIG. 2B is a perspective view of the guidewire and sheath of FIG. 2A depicting the sheath partially retracted as it would be removed proximally after attachment of the guidewire to bone or other tissue.

As depicted in FIG. 2B, the distal end of the guidewire includes a tissue retention member 182 extending from a ball 181. In the embodiment shown, the tissue retention member can be a wire having a drill point or a K-wire (Kirshner wire) which includes a shaft or pin portion having a sharpened distal end 183, much like a drill bit. Positioning the distal end 183 at a selected site on bone and rotating with some pressure applied causes the guidewire to auger into the bone and become affixed at that point. FIG. 2B shows the guidewire with the delivery system being retracted proximally over the guidewire as would be done after the distal tip of the guidewire is embedded in tissue. A strain relief 190 is also visible.

Figure 2C:
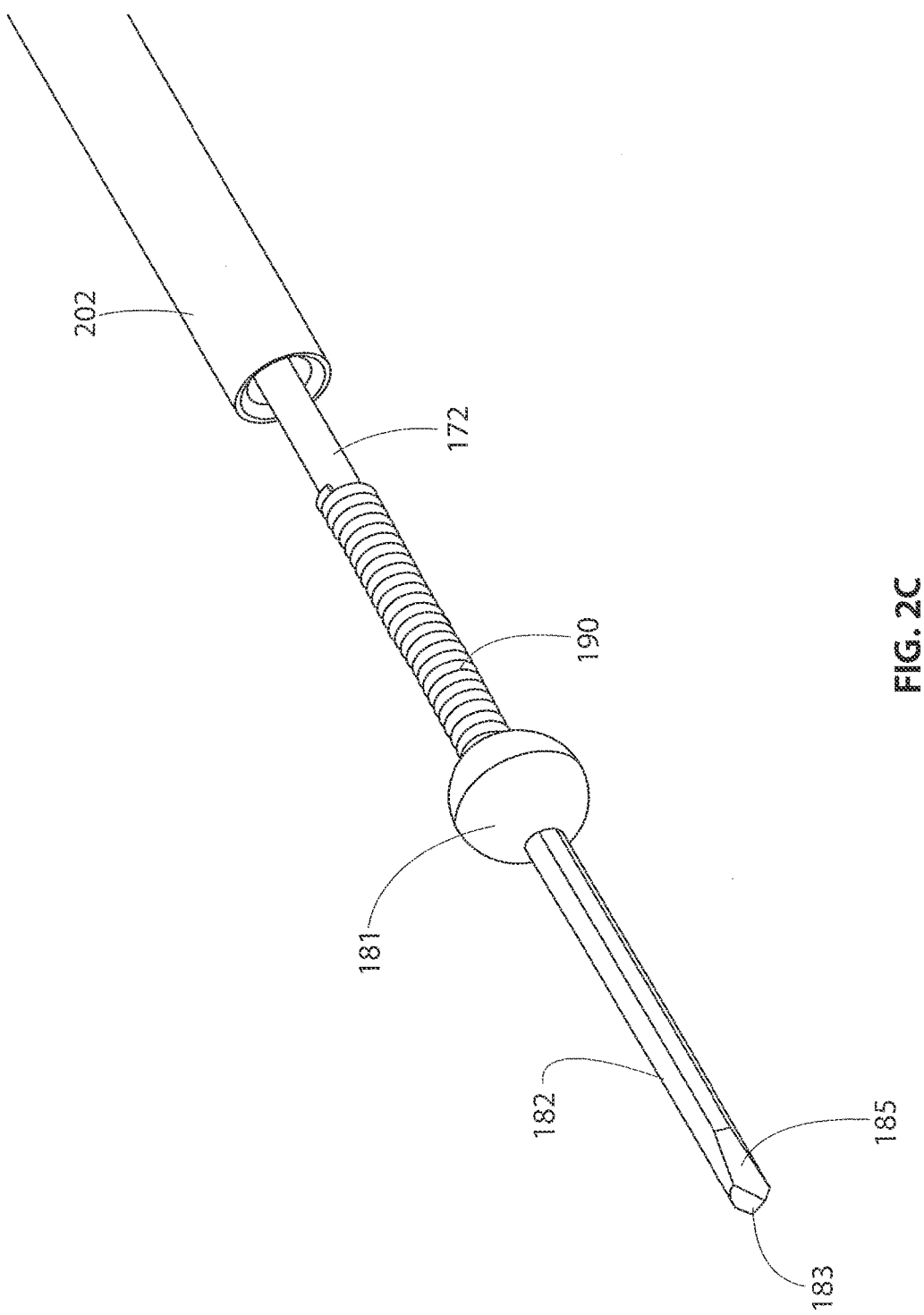
FIG. 2C is partial perspective view of the distal portion of the guidewire of FIG. 2B illustrating a sharpened drill point or K-wire tip for penetrating bone and a strain relief connection to a proximal wire portion.

Referring to FIG. 2C, a closer view of the distal portion of the guidewire 172 is illustrated. The K-wire distal tip includes sharpened edges 185 for cutting into bone or other tissue. Further, the strain relief 190 is shown attached to the weld ball in the form of a spring or coil having the guidewire 172 proximal portion extending from and/or attached to the spring. This configuration allows significant bending of the wire at the spring to allow the delivery system to be tracked to near the ball 181 when in use. The spring also acts as a stop for the implant delivery system when the guidewire port abuts the proximal end of the spring.

Figure 2D:
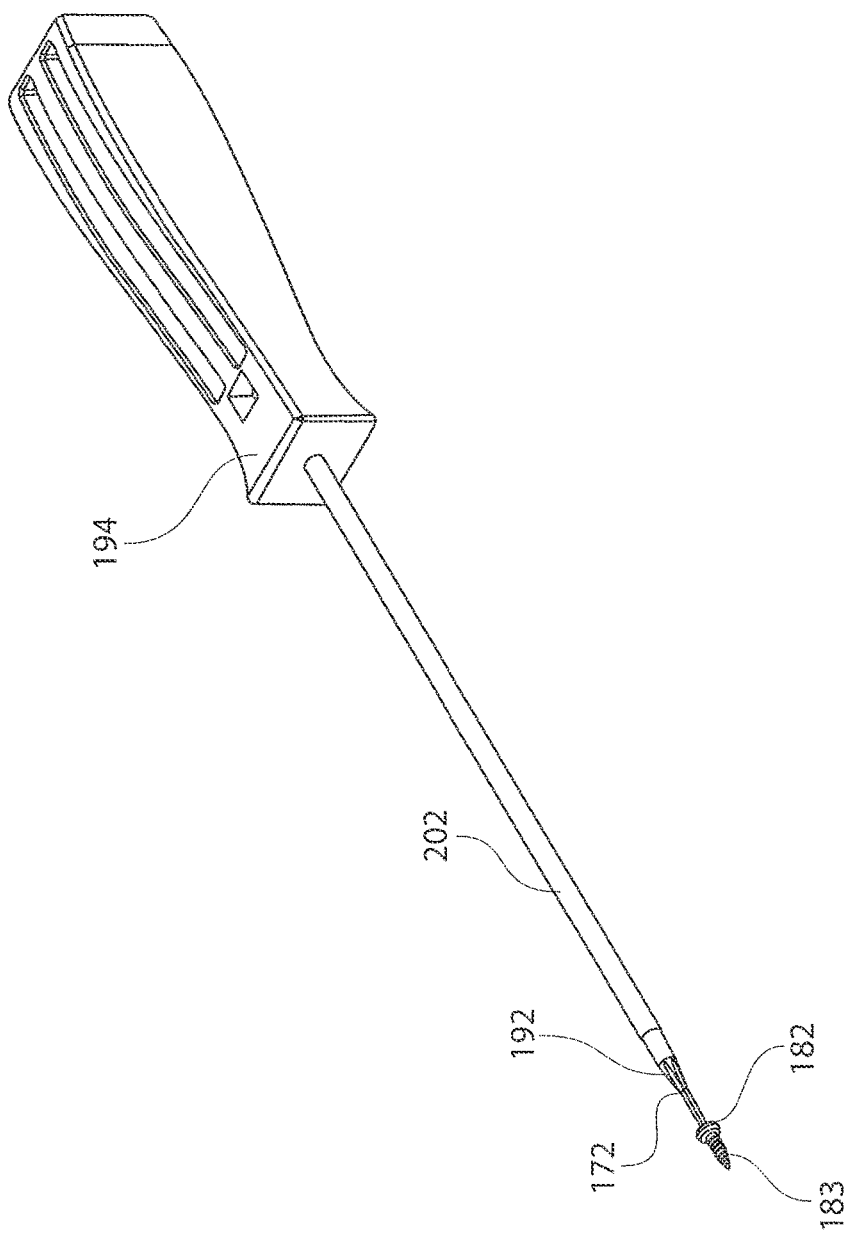
FIG. 2D is a perspective view of an alternative guidewire disposed in a delivery assembly having a distal screw that can be rotated by the sheath to attach to bone or other tissue.

An alternative embodiment of a guidewire and guidewire delivery system is depicted in FIG. 2D. The embodiment is similar to the above described system, however, the tissue retention member 182, 183 is a screw. A strain relief 190 is affixed to the proximal end of the screw and the proximal portion of the guidewire 172 is attached to and extends from the strain relief 190. As illustrated, the guidewire delivery system is essentially a screwdriver with a hollow shaft 202 for receiving the guidewire therein. A distal portion of the hollow shaft 202 engages the head of the screw and a hand can be used to rotate the screw as it augers into bone or other tissue.

Figure 2E:
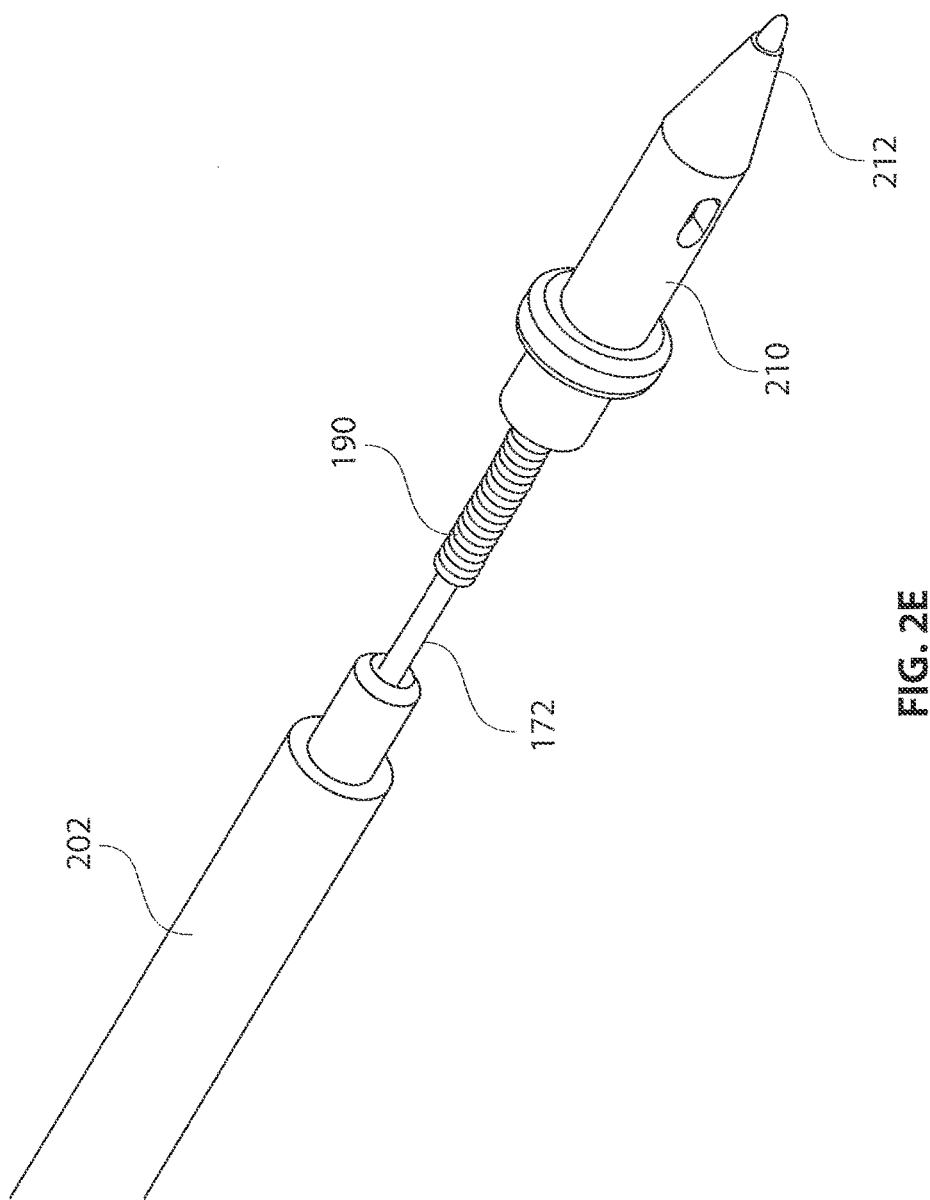
FIG. 2E is a partial perspective view of another alternative guidewire disposed in a sheath having a distal pin that can be hammered into bone or other tissue.

FIG. 2E depicts another alternative guidewire and guidewire delivery system. In this embodiment, the distal end of the guidewire 172 includes a pin 210 that has a distal point 212. The pin has a proximal end attached to a strain relief 190 to which the proximal guidewire portion is attached extending proximally therefrom. The delivery shaft 202 is designed to abut the proximal end of the pin 210 and the system can then be hammered or otherwise forced into bone or other tissue to affix the pin thereto.

As previously disclosed, embodiments of the implant delivery system disclosed herein can be used in conjunction with tissue markers that visually identify anatomical locations at or near a treatment site to assist in proper placement of the implant with the implant delivery system. FIGS. 3A-3D detail one embodiment of a tissue marker system 300. Multiple markers can be used in a given procedure.

Figure 3A:
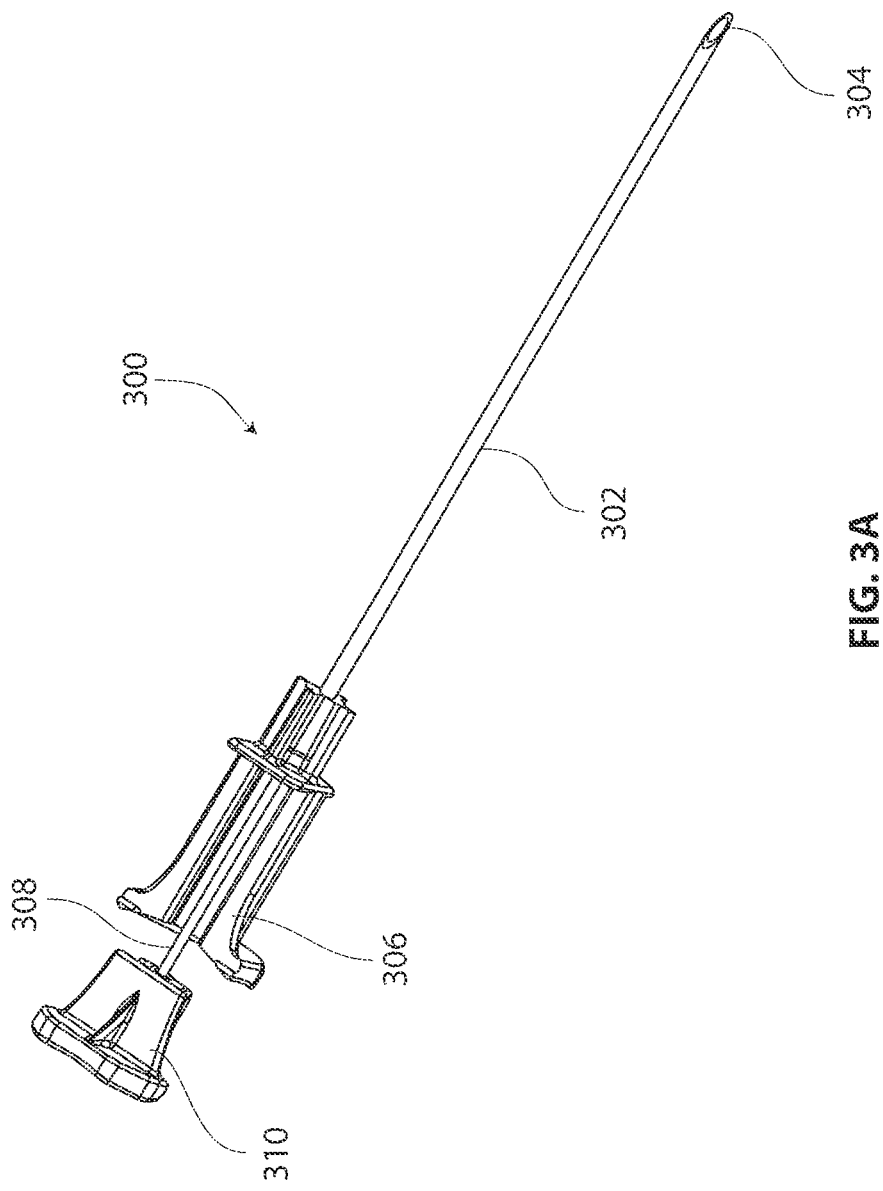
FIG. 3A is perspective view of a marker disposed in a needle-like sheath for insertion into tissue to define a reference point.

Referring first to FIG. 3A, a tissue position marker system 300 is depicted. The tissue marker system 300 includes a delivery sleeve 302 having a lumen 304 therethrough. The delivery sleeve can be a needle-like shaft having a tissue penetrating distal end. A tissue marker 308 is slidably disposed within the lumen 304 of the delivery sleeve 302. The tissue marker 308, in this embodiment has an elongated shaft defining a longitudinal direction. A proximal handle, including a first part 306 and second part 310 are coupled to the tissue marker and delivery sleeve. The second part 310 of the proximal handle can be releasably attached to the tissue marker 308 proximal end so that the second part can be removed to allow the delivery sleeve 302 to be removed proximally over the tissue marker after it is affixed to tissue. The second part 310 can then be re-attached to the proximal end of the marker to aid in removing the marker after the procedure is completed.

FIG. 3B depicts the marker 308 as removed from the delivery sleeve 302. The distal portion of the marker 308 includes a plurality of longitudinally extending arms 312 which are formed into the marker 308 or attached to the distal end of the marker. These arms 312 are better depicted in the illustrations of FIGS. 3C and 3D. When unconstrained, as when the arms 312 are outside of the lumen of the delivery sleeve, the flexible arms project outward from the shaft proximate a distal end thereof, as shown in FIG. 3D. However, when the marker 308 is within the delivery sleeve 302, the lumen walls flex and constrain the arms to extend generally longitudinally and fit therein. In the deployed state outside the delivery sleeve 302, the arms retain the marker's position in tissue, yet can be pulled out without any significant effect on the tissue because the arms will flex to extend generally longitudinally as they are pulled through the tissue. In some embodiments, the arms are flexible nitinol members and the marker can include at least three, and typically four or more arms. The proximal handle can also include means for selectively coupling and decoupling the tissue marker and delivery sleeve to allow easier insertion of the combined assemblies into tissue.

Figure 4A:
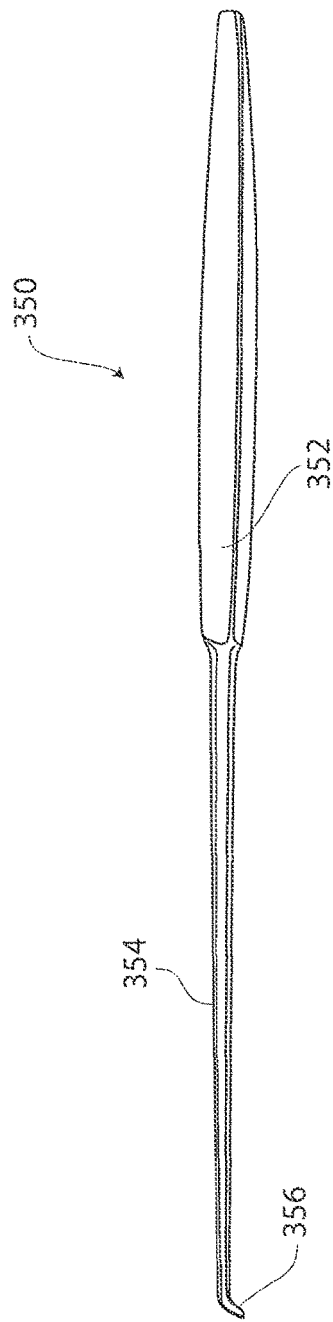
FIG. 4A is a perspective view of an exemplary probe used to observe and measure tissue in a treatment site.
Figure 4B:
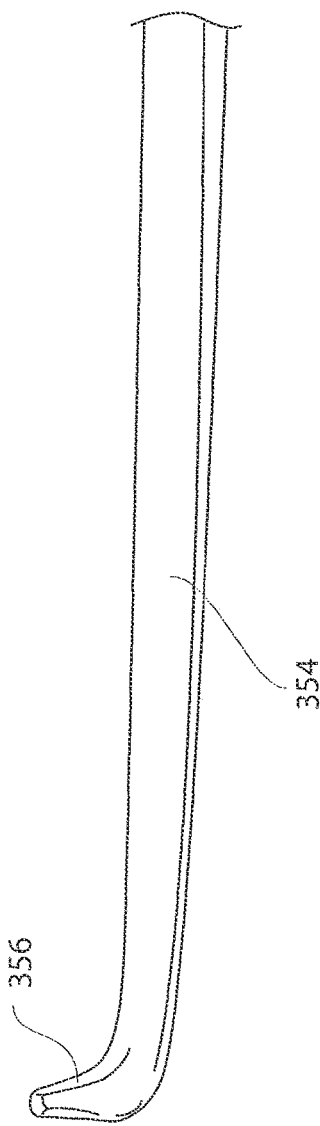
FIG. 4B is a partial perspective view of the distal portion of the probe of FIG. 4A.

As previously disclosed, the systems and devices disclosed herein are used in procedures that can be performed arthroscopically. To better make use of these systems and devices a surgeon can observe, probe and measure features of a treatment site visually to best identify the right implant and fixed locations for placing both the guidewire and/or markers for accurate delivery of the implant. An exemplary probe and measuring tool 350 is depicted in FIGS. 4A and 4B. The probe includes an elongate shaft 352 having a tapered distal portion 354. The tapered distal portion terminates in a hook-shaped distal end 356. Further, the shaft can include ruled markings that can readily be viewed to measure any distance near the treatment site. The probe can be particularly useful in identifying the line of the point of insertion on the supraspinatus tendon to the humeral head by inserting the probe on the articular side of the tendon. The width of the tendon can also be measured in this way for selecting a proper implant size. The probe disclosed is one example of a tool to assist in identifying anatomical points for placement of a guidewire, markers and a delivery system. It is recognized that other tools can be utilized with the delivery system.

Figure 5:
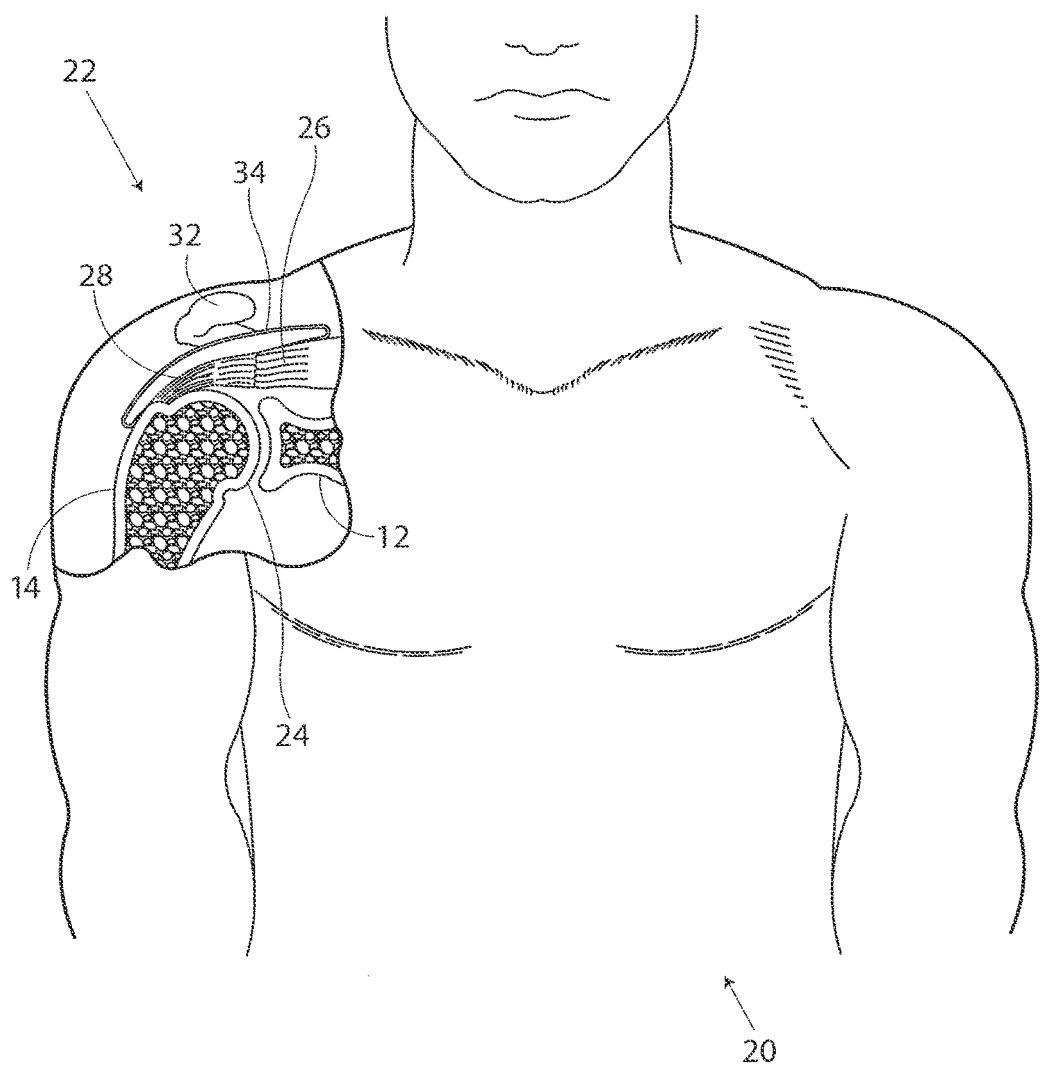
FIG. 5 is a stylized anterior view of a patient with the shoulder being shown in cross-section for purposes of illustration.

Next referring to FIG. 5, an exemplary use or application of the implant delivery system of the present disclosure is described. FIG. 5 is a stylized anterior view of a patient 20. For purposes of illustration, a shoulder 22 of patient 20 is shown in cross-section in FIG. 5. Shoulder 22 includes a humerus 14 and a scapula 12. In FIG. 5, a head 24 of humerus 14 can be seen mating with a glenoid fossa of scapula 12 at a glenohumeral joint. The glenoid fossa comprises a shallow depression in scapula 12. The movement of humerus 14 relative to scapula 12 is controlled by a number of muscles including: the deltoid, the supraspinatus, the infraspinatus, the subscapularis, and the teres minor. For purposes of illustration, only the supraspinatus 26 is shown in FIG. 5.

With reference to FIG. 5, a distal tendon 28 of the supraspinatus 26 meets humerus 14 at an insertion point. Scapula 12 of shoulder 22 includes an acromion 32. A subacromial bursa 34 is shown extending between acromion 32 of scapula 12 and head 24 of humerus 14. Subacromial bursa 34 is shown overlaying supraspinatus 26 as well as supraspinatus tendon 28 and a portion of humerus 14. Subacromial bursa 34 is one of the hundreds of bursae found the human body. Each bursa comprises a fluid filled sac. The presence of these bursae in the body reduces friction between bodily tissues.

The exemplary implant delivery system described herein may be used to position and deploy sheet-like implants to various target tissues throughout the body. The shoulder depicted in FIG. 5 is one example where a tendon repair implant may be affixed to one or more bones associated with an articulating joint, such as the glenohumeral joint. Additionally, the tendon repair implant may be affixed to one or more tendons to be treated. The tendons to be treated may be torn, partially torn, have internal micro-tears, be untorn, and/or be thinned due to age, injury or overuse. Applicants believe that the methods and apparatus of the present application and related devices may provide very beneficial therapeutic effect on a patient experiencing joint pain believed to be caused by partial thickness tears and/or internal microtears. By applying a tendon-repair implant early before a full tear or other injury develops, the implant may cause the tendon to thicken and/or at least partially repair itself, thereby avoiding more extensive joint damage, pain, and the need for more extensive joint repair surgery.

Figure 6:
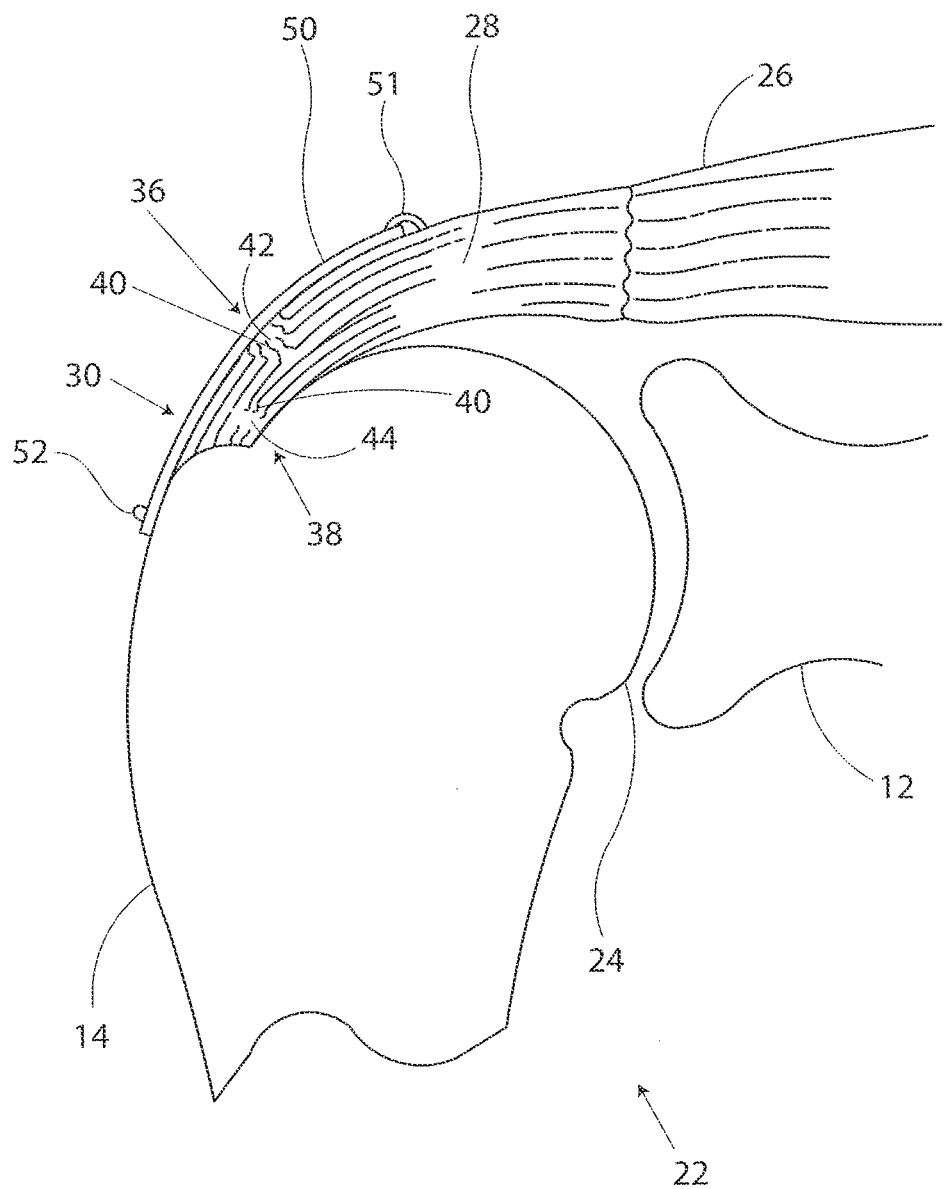
FIG. 6 is a stylized view of a shoulder depicting the head of the humerus shown mating with the glenoid fossa of the scapula at a glenohumeral joint and a sheet-like material is affixed to the tendon.

FIG. 6 is a stylized anterior view of a shoulder 22 including a humerus 14 and a scapula 12. In FIG. 6, a head 24 of humerus 14 is shown mating with a glenoid fossa of scapula 12 at a glenohumeral joint. A supraspinatus 26 is also shown in FIG. 6. This muscle, along with others, controls the movement of humerus 14 relative to scapula 12. A distal tendon 28 of supraspinatus 26 meets humerus 14 at an insertion point 30.

As depicted in FIG. 6, distal tendon 28 includes a first damaged portion 36. A number of loose tendon fibers 40 in first damaged portion 36 are visible in FIG. 6. First damaged portion 36 includes a first tear 42 extending partially through distal tendon 28. First tear 42 may therefore be referred to as a partial thickness tear. With reference to FIG. 6, first tear 42 begins on the side of distal tendon 28 facing the subacromial bursa (shown in the previous Figure) and ends midway through distal tendon 28. Accordingly, first tear 42 may be referred to as a bursal side tear.

With reference to FIG. 6, distal tendon 28 includes a second damaged portion 38 located near insertion point 30. As illustrated, second damaged portion 38 of distal tendon 28 has become frayed and a number of loose tendon fibers 40 are visible. Second damaged portion 38 of distal tendon 28 includes second tear 44. Second tear 44 begins on the side of distal tendon 28 facing the center of the humeral head 24. Accordingly, second damaged portion 38 may be referred to as an articular side tear.

FIG. 6 illustrates a sheet-like implant 50 has been placed over the bursal side of distal tendon 28. The sheet-like implant 50 is affixed to distal tendon 28 by a plurality of tendon staples 51. Sheet-like implant 50 is affixed to humerus 14 by a plurality of bone staples 100. Sheet-like implant 50 extends over insertion point 30, first tear 42 and second tear 44. Some useful methods in accordance with this detailed description may include placing a tendon repair implant on the bursal side of a tendon regardless of whether the tears being treated are on the bursal side, articular side or within the tendon. In some cases the exact location and nature of the tears being treated may be unknown. A tendon repair implant may be applied to the bursal side of a tendon to treat shoulder pain that is most likely caused by one or more partial thickness tears in the tendon.

Figure 7A:
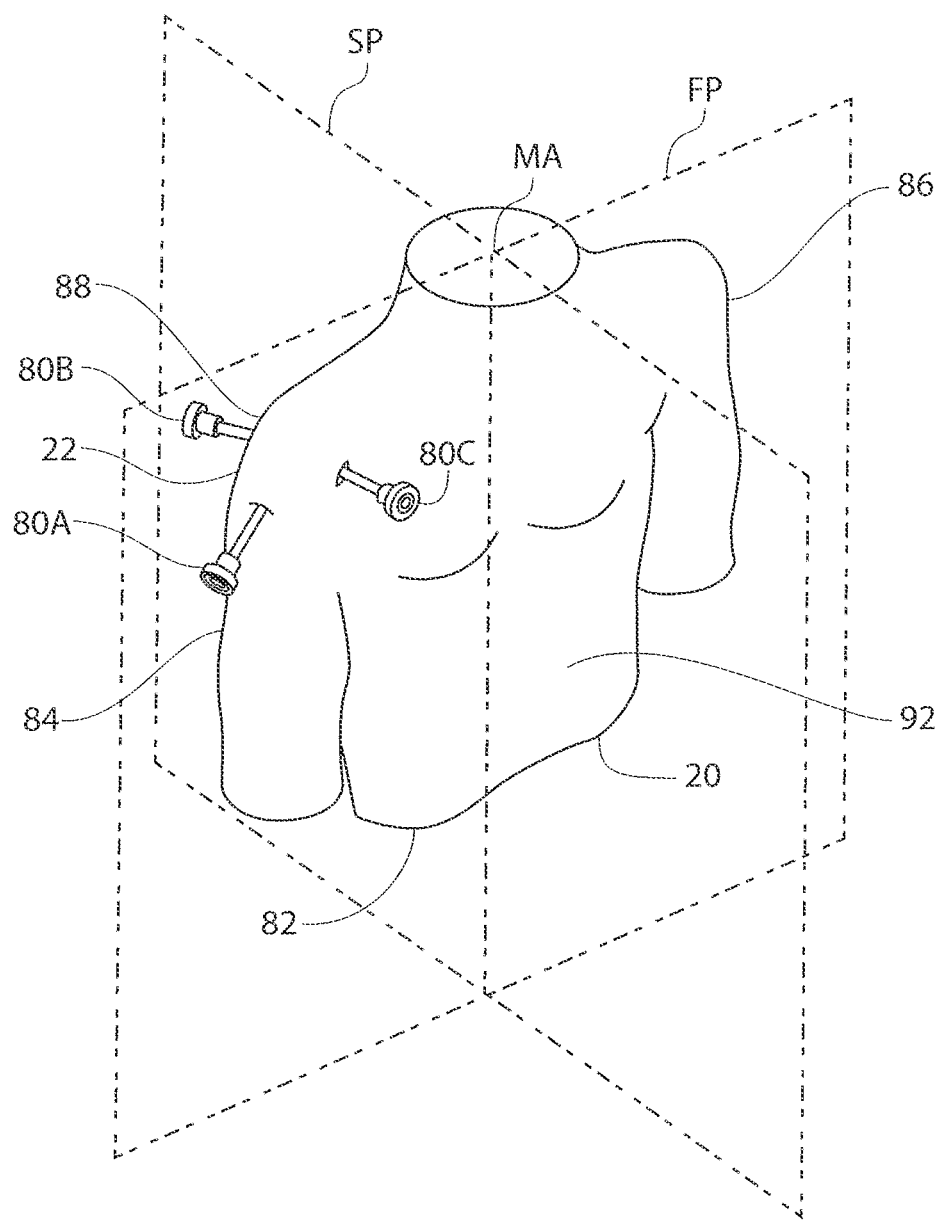
FIG. 7A is a stylized perspective view showing a portion of the body of a human patient divided into quadrants by planes for descriptive purposes.

FIG. 7A is a stylized perspective view showing a portion of the body 82 of a human patient 20. Body 82 includes a shoulder 22. In the exemplary embodiment of FIG. 7A, a plurality of cannulas is positioned to access a treatment site within shoulder 22. In some cases, shoulder 22 may be inflated by pumping a continuous flow of saline through shoulder 22 to create a cavity proximate the treatment site. The cannulas shown in FIG. 7A include a first cannula 80A, a second cannula 80B and a third cannula 80C.

In FIG. 7A, a sagital plane SP and a frontal plane FP are shown intersecting body 82. Sagital plane SP and frontal plane FP intersect one another at a medial axis MA of body 82. With reference to FIG. 7A, sagital plane SP bisects body 82 into a right side 84 and a left side 86. Also with reference to FIG. 7A, frontal plane FP divides body 82 into an anterior portion 92 and a posterior portion 88. Sagital plane SP and a frontal plane FP are generally perpendicular to one another. These planes and portions are used to describe the procedures used in exemplary embodiments.

First cannula 80A is accessing a treatment site within shoulder 22 using a lateral approach in which first cannula 80A pierces the outer surface of right side 84 of body 82. The term lateral approach could also be used to describe situations in which an instrument pierces the outer surface of left side 86 of body 82. Second cannula 80B is accessing a treatment site within shoulder 22 using a posterior approach in which second cannula 80B pierces the outer surface of posterior portion 88 of body 82. Third cannula 80C is accessing a treatment site within shoulder 22 using an anterior approach in which third cannula 80C pierces the outer surface of anterior portion 92 of body 82.

Figure 7B:
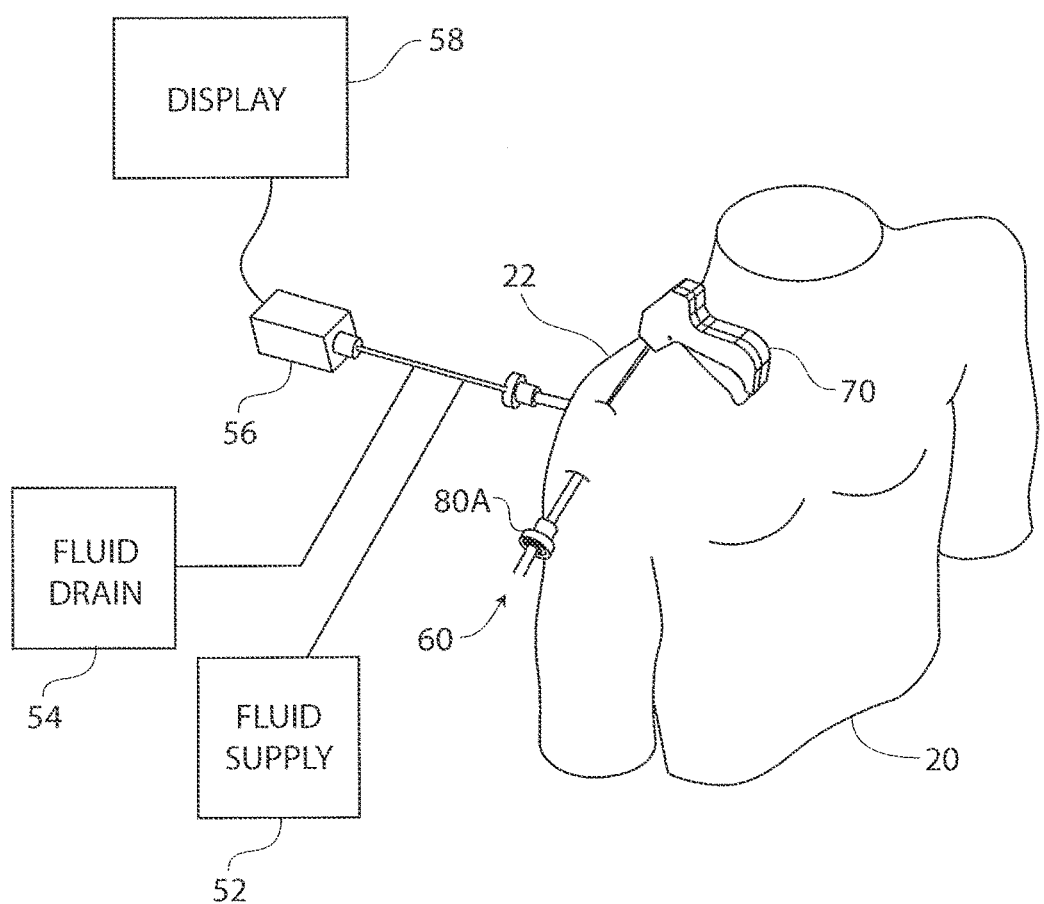
FIG. 7B is a stylized perspective view illustrating an exemplary procedure for arthroscopic treatment of a shoulder of a patient in accordance with one embodiment of the disclosure.

FIG. 7B is a stylized perspective view illustrating an exemplary procedure for treating a shoulder 22 of a patient 20. The procedure illustrated in FIG. 7B may include, for example, fixing tendon repair implants to one or more tendons of shoulder 22. The tendons treated may be torn, partially torn, have internal micro-tears, be untorn, and/or be thinned due to age, injury or overuse.

Shoulder 22 of FIG. 7B has been inflated to create a cavity therein. A fluid supply 52 is pumping a continuous flow of saline into the cavity. This flow of saline exits the cavity via a fluid drain 54. A camera 56 provides images from inside the cavity. The images provided by camera 56 may be viewed on a display 58.

Camera 56 may be used to visually inspect the tendons of shoulder 22 for damage. A tendon repair implant in accordance with this disclosure may be affixed to a bursal surface of the tendon regardless of whether there are visible signs of tendon damage. Applicants believe that the methods and apparatus of the present application and related devices may provide very beneficial therapeutic effect on a patient experiencing joint pain believed to be caused by internal microtears, but having no clear signs of tendon tears. By applying a tendon repair implant early before a full tear or other injury develops, the implant may cause the tendon to thicken and/or at least partially repair itself, thereby avoiding more extensive joint damage, pain, and the need for more extensive joint repair surgery.

An implant delivery system 60 can be seen extending from shoulder 22 in FIG. 7B. Implant delivery system 60 is extending through a first cannula 80A. In certain embodiments, first cannula 80A can access a treatment site within shoulder 22 using a lateral approach in which first cannula 80A pierces the outer surface of a right side of the patient's body. In some cases a physician may choose not to use a cannula in conjunction with implant delivery system 60. When that is the case, the implant delivery system may be advanced through tissue. Implant delivery system 60 comprises a sheath that is affixed to a handle. The sheath defines a lumen and a distal opening fluidly communicating with the lumen. In the embodiment of FIG. 7B, the distal opening of the sheath has been placed in fluid communication with the cavity created in shoulder 22.

A tendon repair implant is at least partially disposed in the lumen defined by the sheath of implant delivery system 60. Implant delivery system 60 can be used to place the tendon repair implant inside shoulder 22. In some embodiments, the tendon repair implant is folded into a compact configuration when inside the lumen of the sheath. When this is the case, implant delivery system 60 may be used to unfold the tendon repair implant into an expanded shape. Additionally, implant delivery system 60 can be used to hold the tendon repair implant against the tendon.

The tendon repair implant may be affixed to the tendon while it is held against the tendon by implant delivery system 60. Various attachment elements may be used to fix the tendon-repair implant to the tendon. Examples of attachment elements that may be suitable in some applications include sutures, tissue anchors, bone anchors, and staples. In the exemplary embodiment of FIG. 7B, the shaft of a fixation tool 70 is shown extending into shoulder 22. In one exemplary embodiment, fixation tool 70 is capable of fixing the tendon repair implant to the tendon and bone with one or more staples while the tendon repair implant may be held against the tendon by implant delivery system 60.

As previously stated, the implant delivery system 60 can be used to deliver any sheet-like implant. A tendon repair implant 50 may comprise, for example, various sheet-like structures without deviating from the spirit and scope of the present detailed description. In some useful embodiments, the sheet-like structure may comprise a plurality of fibers. The fibers may be interlinked with one another. When this is the case, the sheet-like structure may comprise a plurality of apertures comprising the interstitial spaces between fibers. Various processes may be used to interlink the fibers with one another. Examples of processes that may be suitable in some applications including weaving, knitting, and braiding. In some embodiments, the sheet-like structure may comprise a laminate including multiple layers of film with each layer of film defining a plurality of micro-machined or formed holes. The sheet-like structure of the tendon repair implant may also comprise a reconstituted collagen material having a porous structure. Additionally, the sheet-like structure of the tendon repair implant may also comprise a plurality of electro-spun nanofiber filaments forming a composite sheet. Additionally, the sheet-like structure may comprise a synthetic sponge material that defines a plurality of pores. The sheet-like structure may also comprise a reticulated foam material. Reticulated foam materials that may be suitable in some applications are available from Biomerix Corporation of Fremont, Calif. which identifies these materials using the trademark BIOMATERIAL™. The sheet-like structure may be circular, oval, oblong, square, rectangular, or other shape configured to suit the target anatomy. Various attachment elements may be used to fix tendon repair implant 50 to distal tendon 28 without deviating from the spirit and scope of this detailed description. Examples of attachment elements that may be suitable in some applications include sutures, tissue anchors, bone anchors, and staples. In the embodiment of FIG. 6, sheet-like implant 50 is affixed to distal tendon 28 by a plurality of tendon staples 51. Sheet-like implant 50 is affixed to humerus 14 by a plurality of bone staples 52. Details of exemplary tendon staples may be found in commonly assigned co-pending applications: U.S. application Ser. No. 12/684,774 filed Jan. 8, 2010; U.S. application Ser. No. 12/729,029 filed Mar. 22, 2010; U.S. application Ser. No. 12/794,540 filed Jun. 4, 2010; U.S. application Ser. No. 12/794,551 filed on Jun. 4, 2010; U.S. application Ser. No. 12/794,677 filed on Jun. 4, 2010; and U.S. application Ser. No. 61/443,180 filed on Feb. 15, 2011, the disclosures of which are incorporated herein by reference. Exemplary bone staples are described in commonly assigned co-pending applications: U.S. application Ser. No. 61/577,626 filed Dec. 19, 2011; U.S. application Ser. No. 61/577,632 filed Dec. 19, 2011 and U.S. application Ser. No. 61/577,635 filed Dec. 19, 2011, the disclosures of which are incorporated herein by reference. Exemplary staples in many of the above applications may be used for anchoring in both soft tissue and in bone.

Figure 8A:
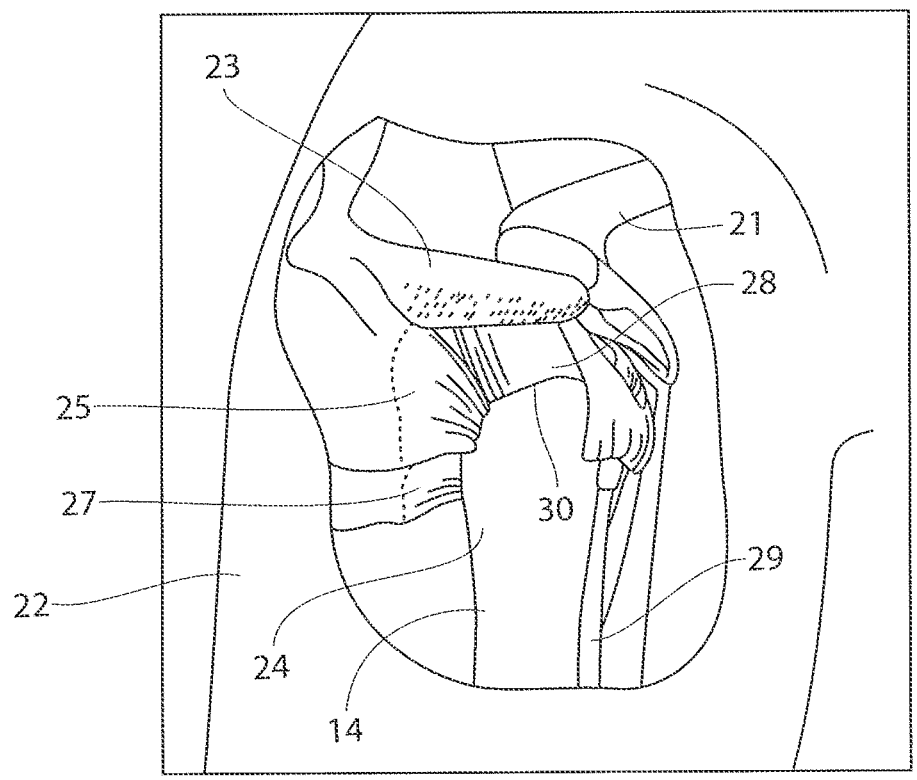
FIG. 8A is a perspective view of a portion of the shoulder with parts removed to illustrate the supraspinatus tendon in relation to other anatomical features.
Figure 8B:
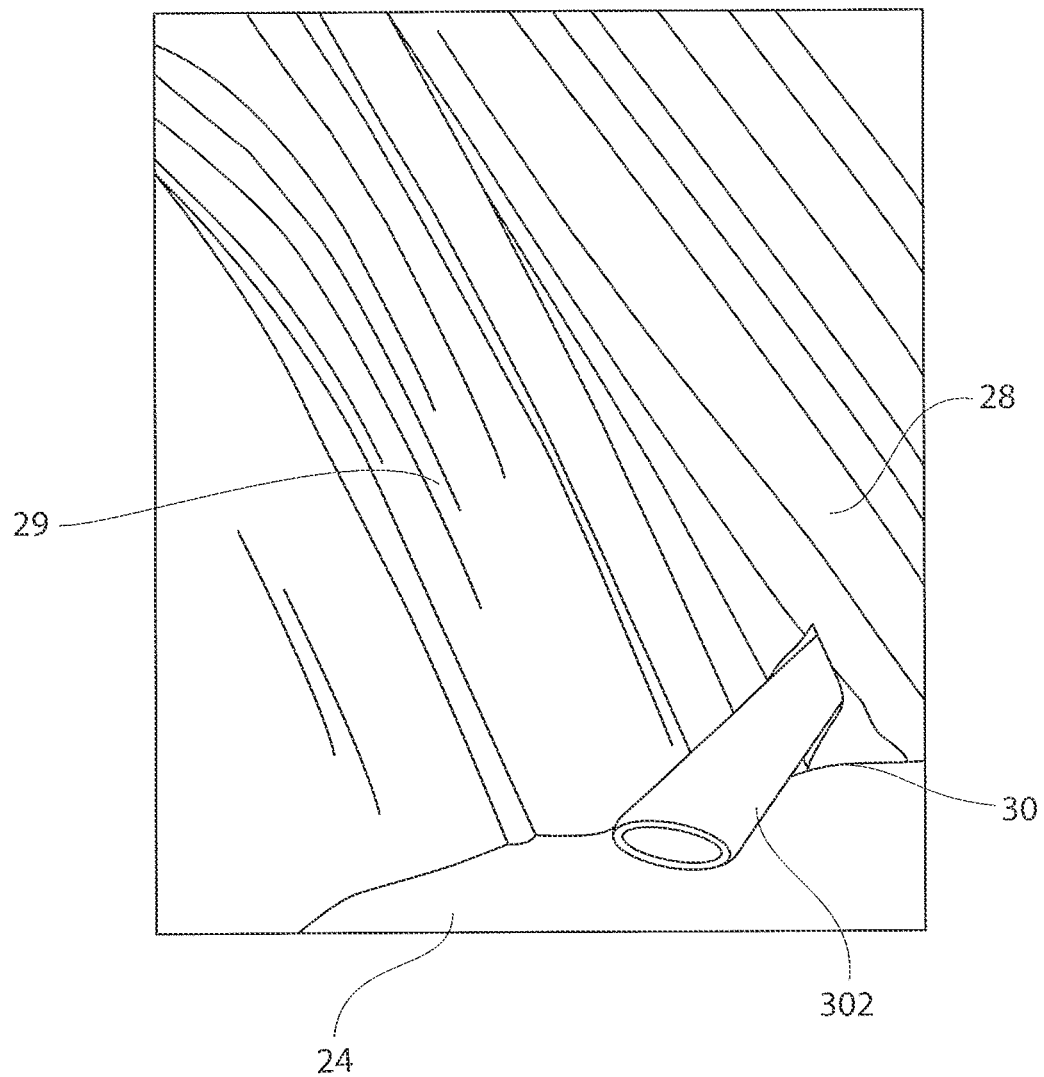
FIG. 8B is a partial perspective view of the articular side of the supraspinatus tendon illustrating the position relative to the biceps tendon and a marker inserted from the bursal side to identify the location of the biceps tendon which is not visible from the bursal side.
Figure 8C:
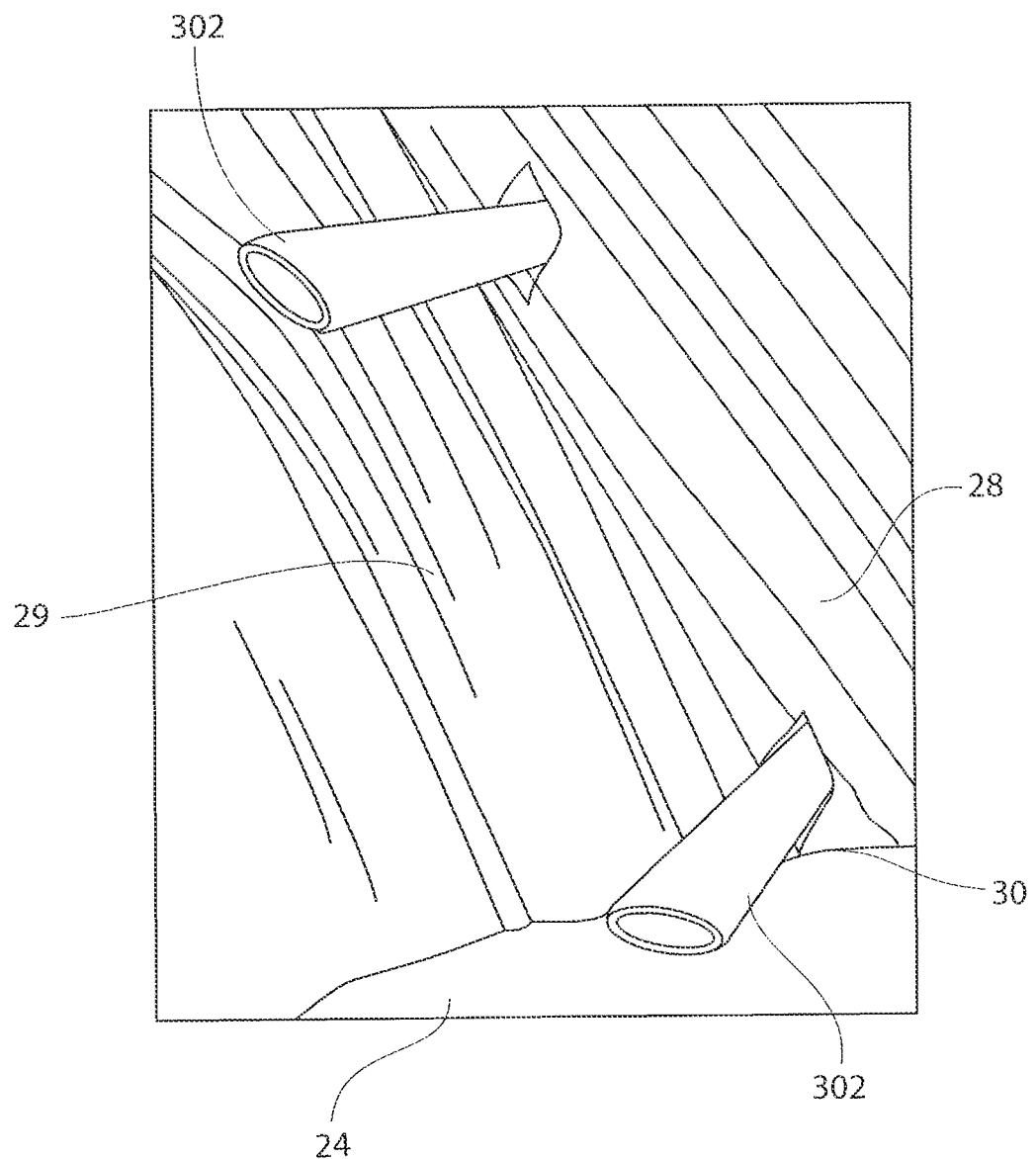
FIG. 8C is another partial perspective view of the articular side of the supraspinatus tendon as shown in FIG. 8B with a second marker inserted to delineate the biceps tendon over its length which is not visible from the bursal side.
Figure 8D:
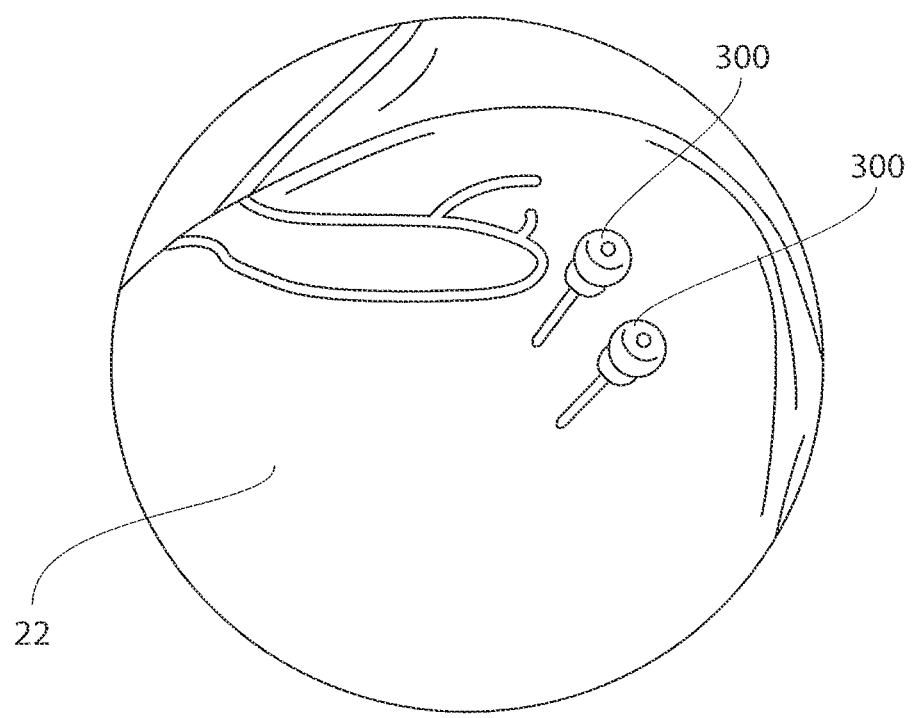
FIG. 8D is a partial perspective view of the shoulder showing the two markers of FIG. 8C as they extend proximally from a point of insertion in the skin.
Figure 8E:
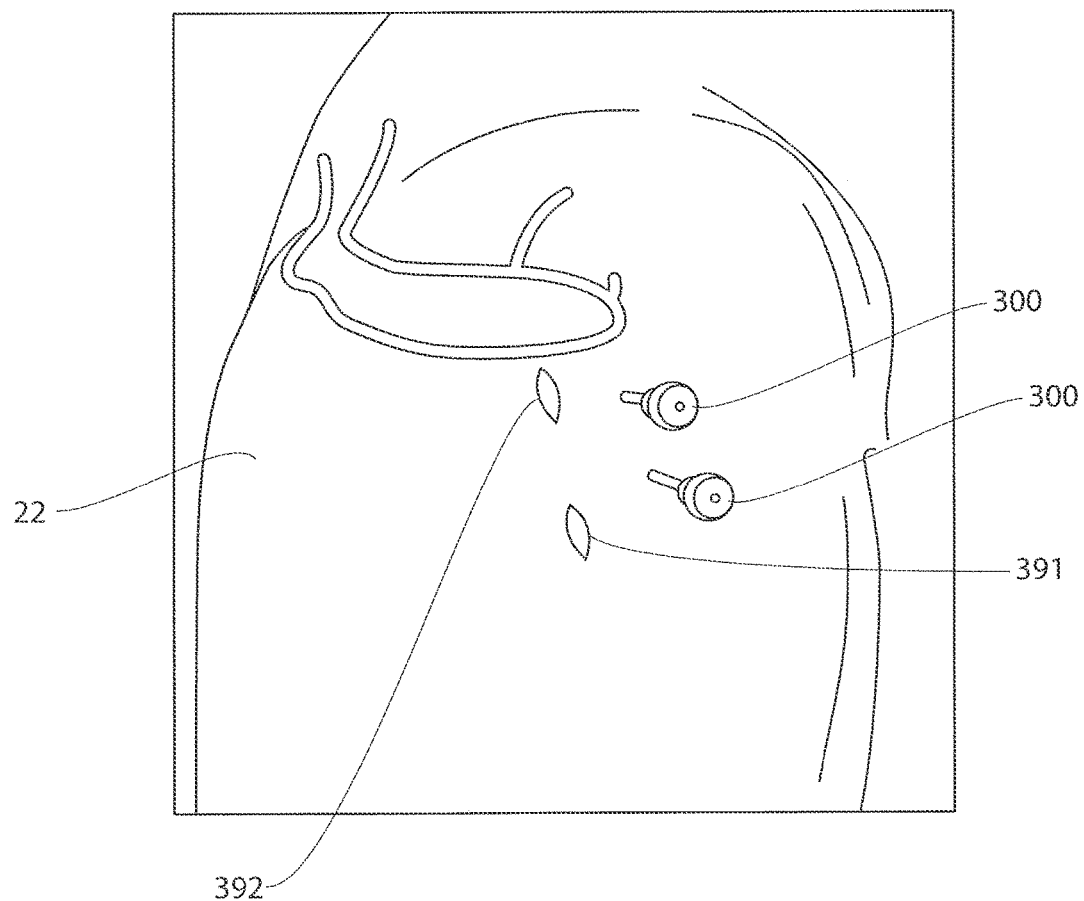
FIG. 8E is a partial perspective view of the shoulder of FIG. 8D with the inclusion of two portal incisions made relative to the markers.
Figure 8F:
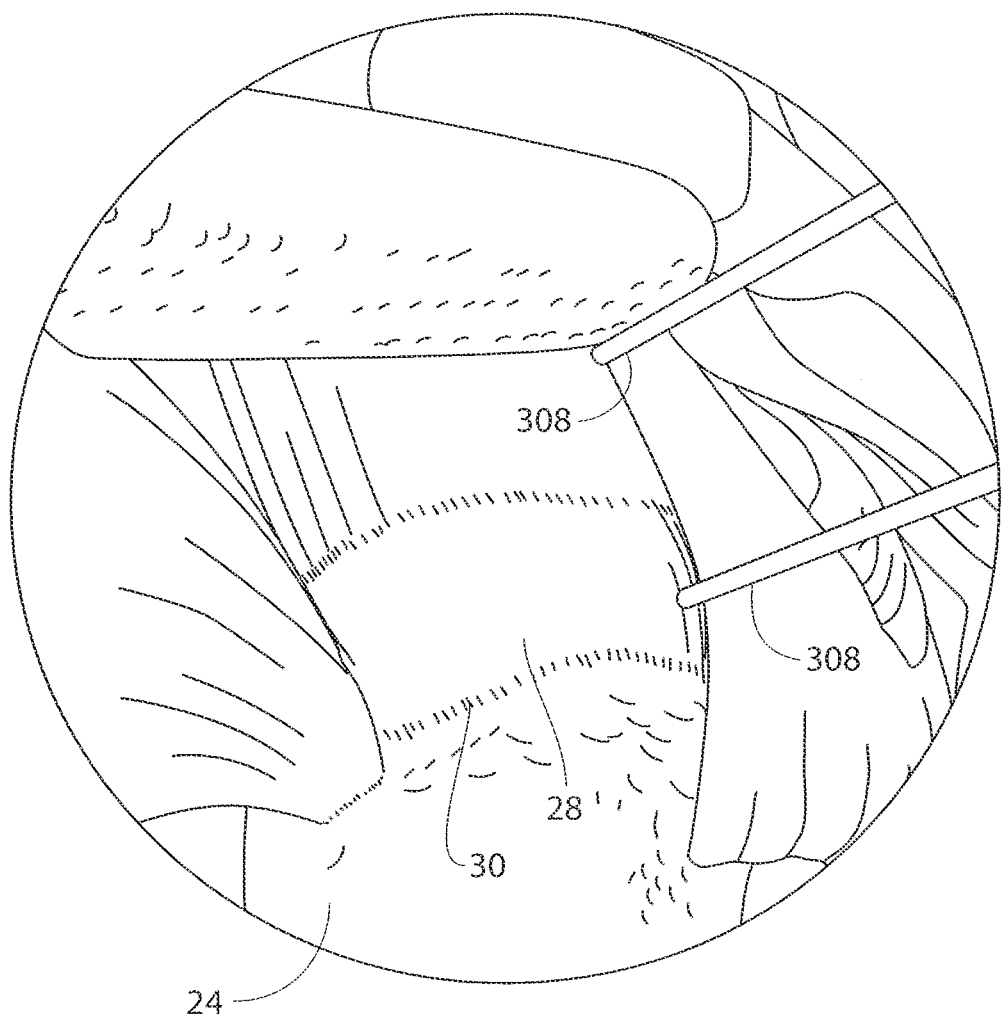
FIG. 8F is a partial perspective view of the shoulder of FIG. 8A depicting the two markers from the bursal side of the tendon as they extend therethrough and would be seen during arthroscopic placement of an implant.
Figure 8G:
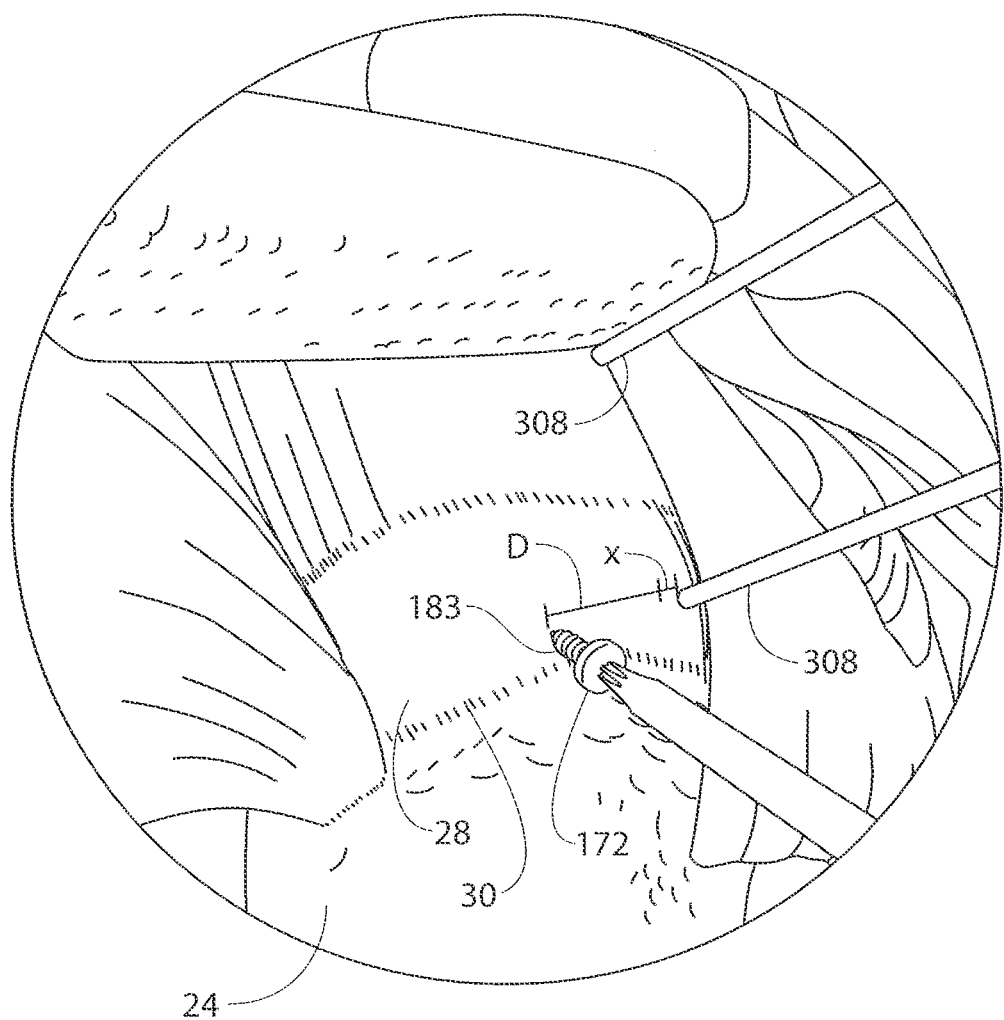
FIG. 8G is a partial perspective view of the shoulder of FIG. 8F illustrating the placement of a guidewire relative to the markers.
Figure 8H:
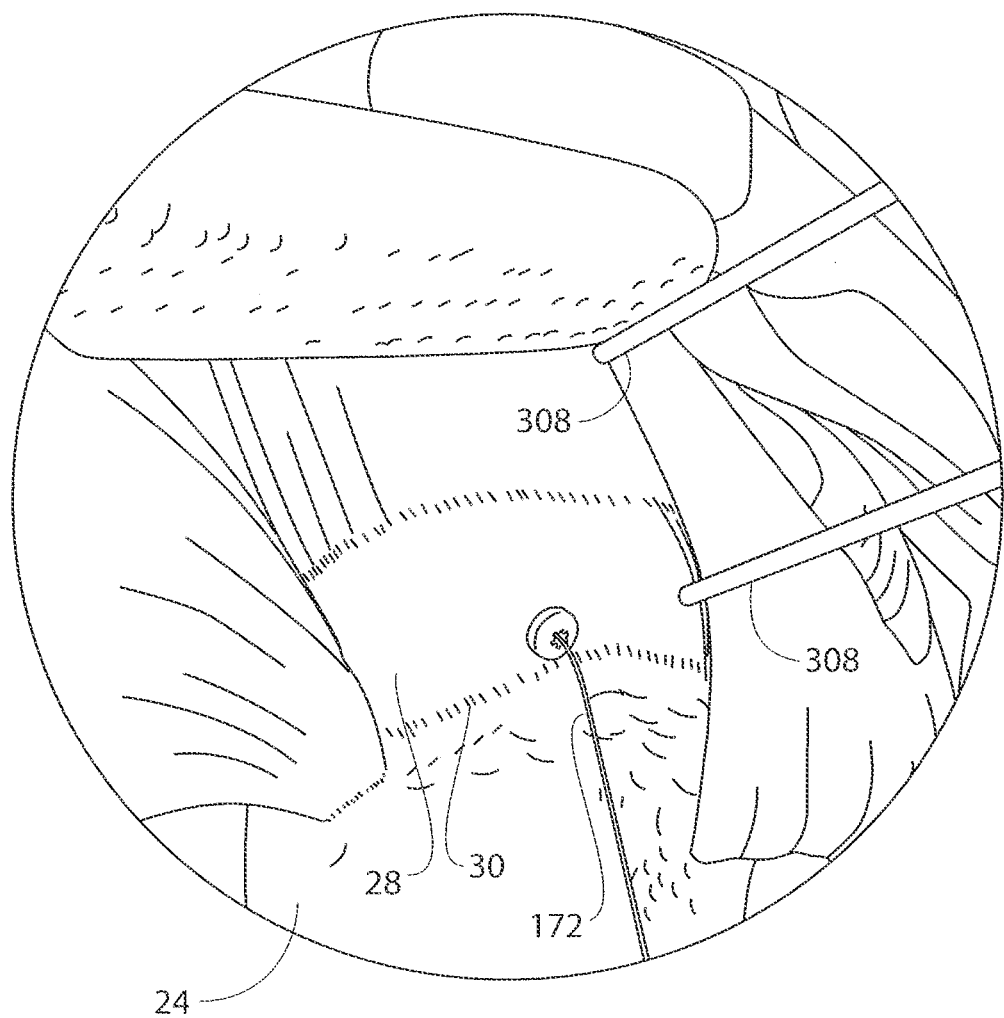
FIG. 8H is a partial perspective view illustrating a guidewire as affixed to bone relative to the markers.
Figure 8I:
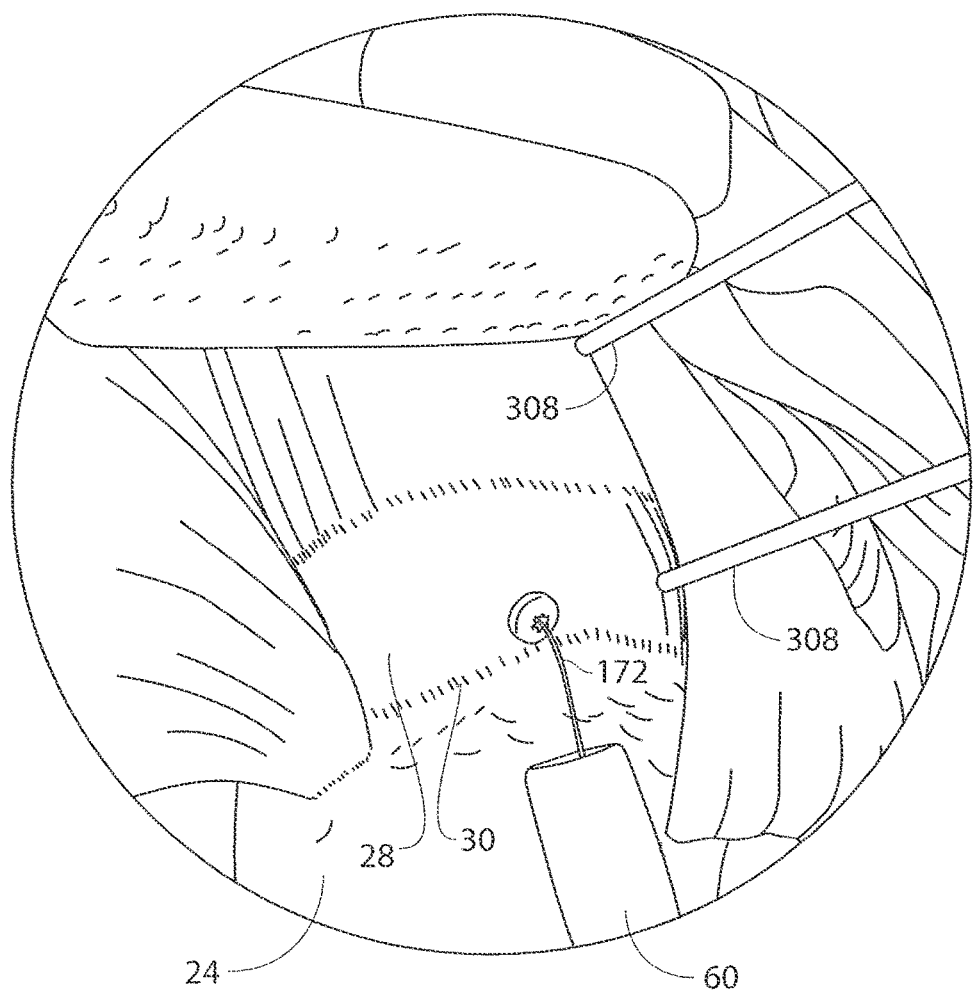
FIG. 8I is a partial perspective view of the shoulder of FIG. 8H with an implant delivery system distal sheath illustrated as guided over the wire.
Figure 8J:
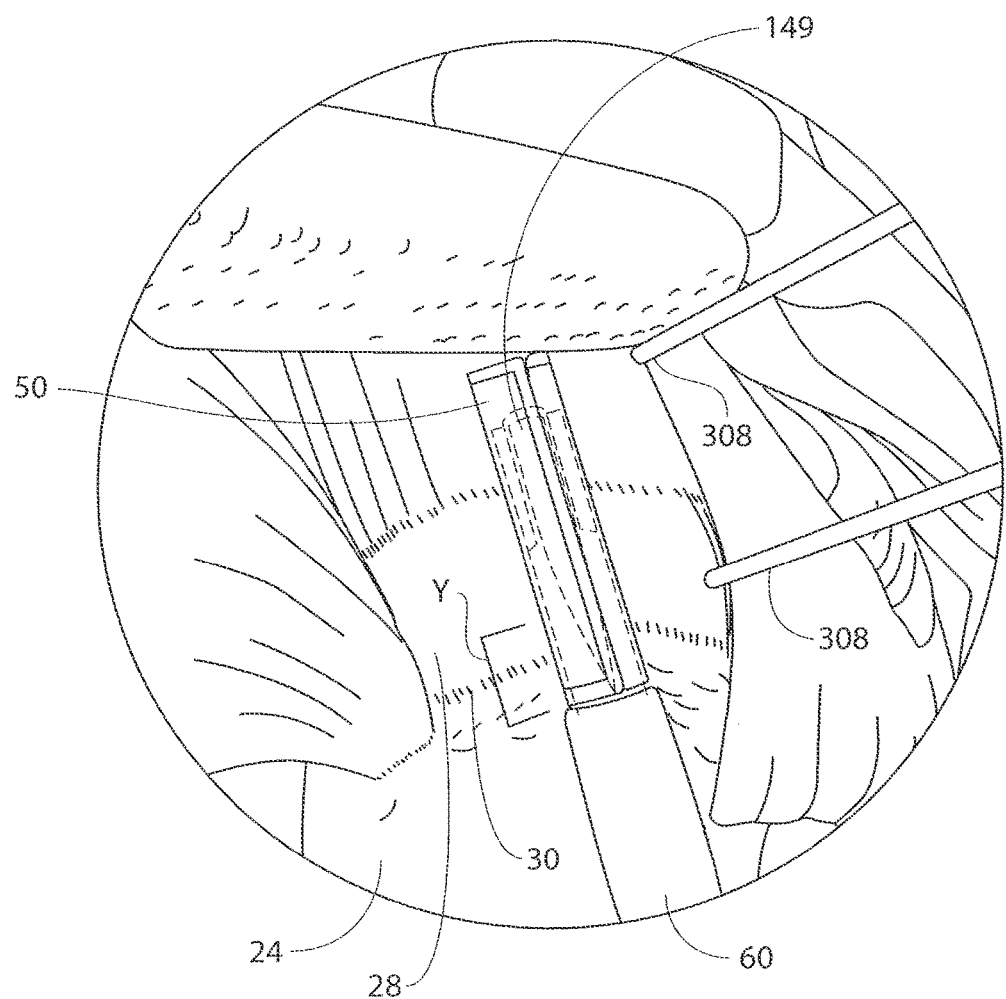
FIG. 8J is a partial perspective view of the shoulder of FIG. 8I illustrating the extension of an implant retention assembly from the sheath.
Figure 8K:
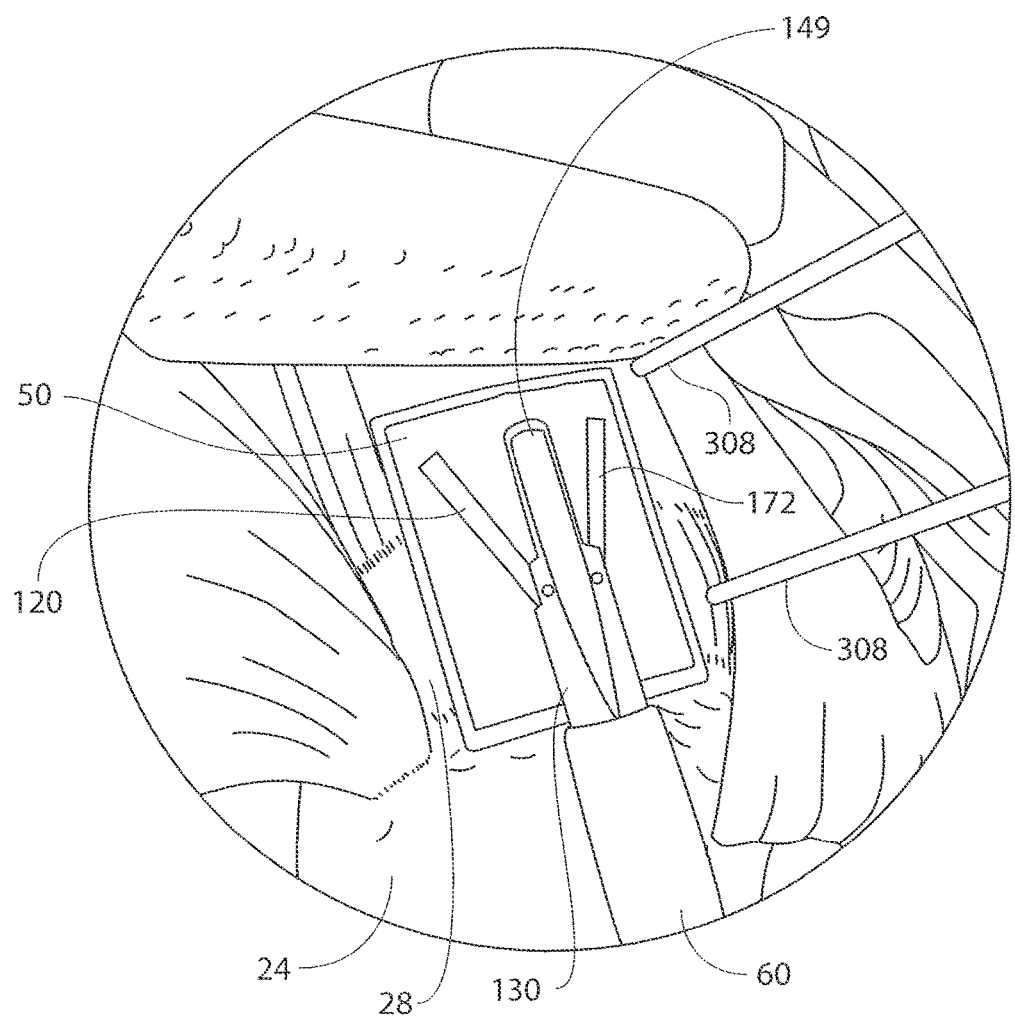
FIG. 8K is a partial perspective view of the shoulder of FIG. 8J illustrating the deployment of an implant spreader assembly and positioning of the implant relative to the markers.
Figure 8L:
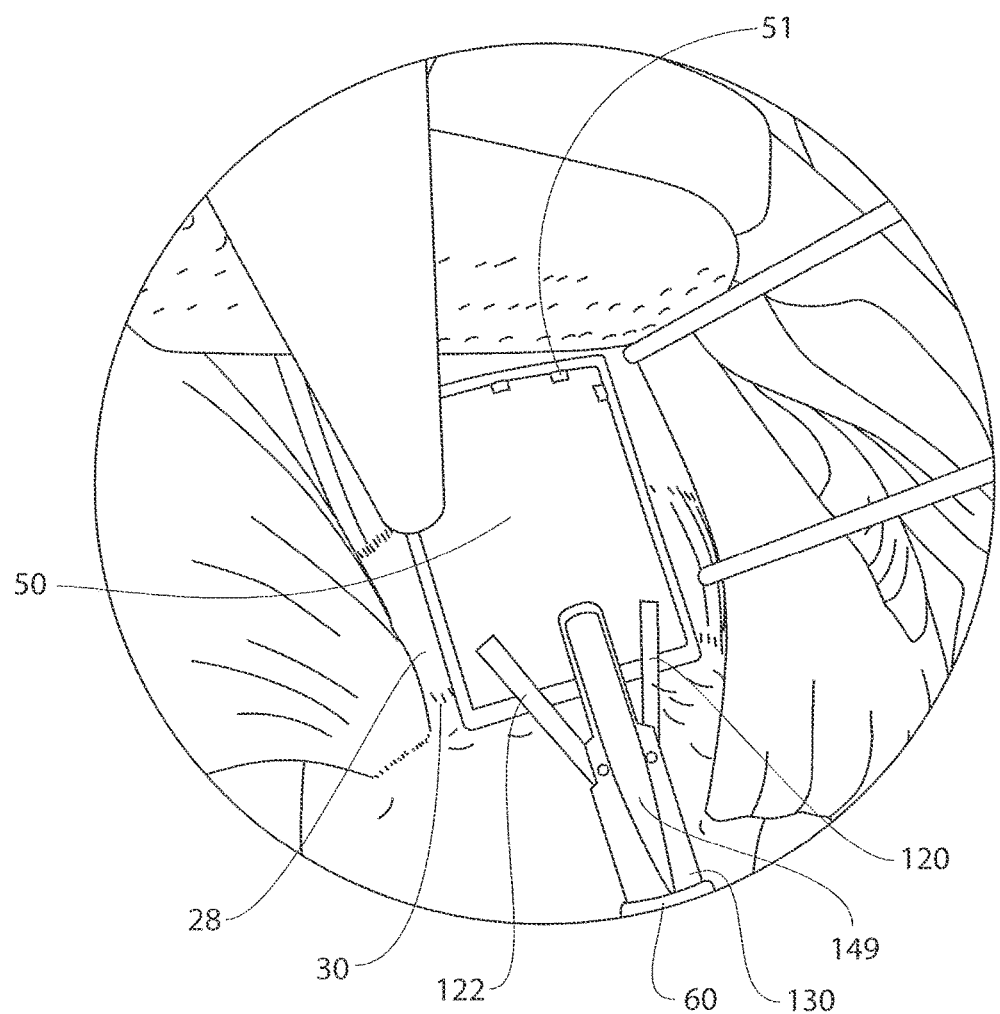
FIG. 8L is a partial perspective view of the shoulder of FIG. 8K depicting partial retraction of the implant delivery system as the implant is affixed by staples to the tendon.
Figure 8M:
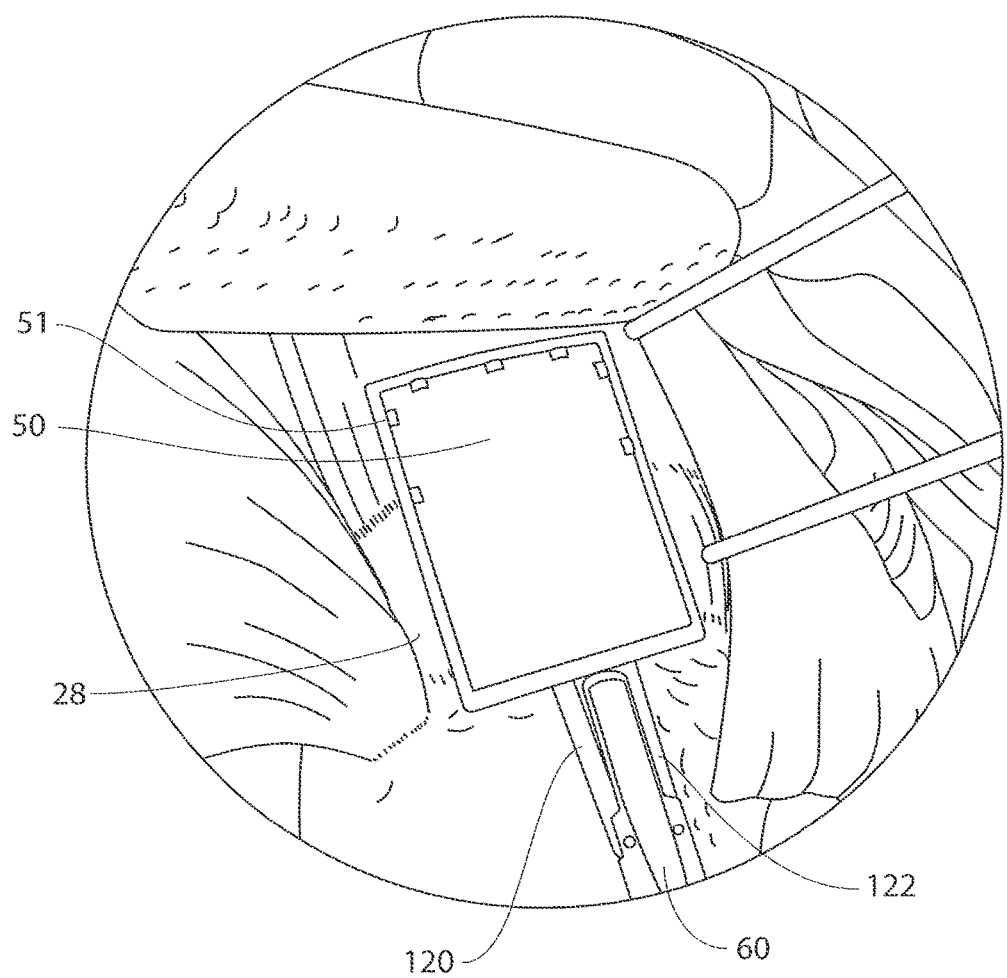
FIG. 8M is a partial perspective view of the shoulder of FIG. 8L depicting the closing of the implant spreader assembly in conjunction with removal from the shoulder.
Figure 8N:
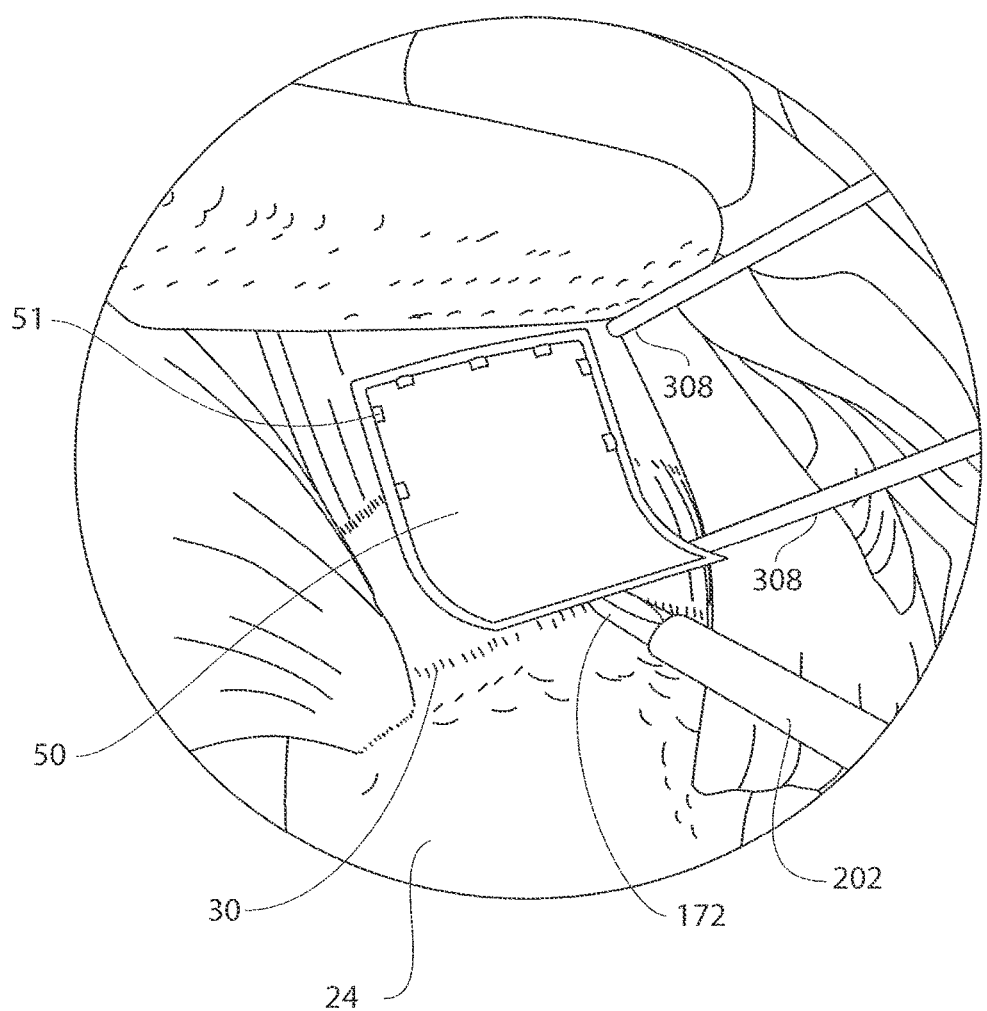
FIG. 8N is a partial perspective view of the shoulder of FIG. 8M depicting removal of the guidewire attachment from the shoulder prior to affixing the proximal portion of the implant to the humeral head.

Referring to FIGS. 8A-8N, a series of step-wise illustrations are provided of exemplary use of the markers, guidewire and implant delivery system as an overall kit for treatment of the supraspinatus tendon of the shoulder. The supraspinatus tendon is used to illustrate one use of the system which may be adapted for use in other areas of the body, as one of skill in the art will readily recognize. In particular, the system is useful in areas of the body requiring accurate placement of the implant relative to other anatomical structures as the system is guided to a marked first position by the guidewire and rotated to proper orientation relative to at least one, and at times two other markers of anatomical structure.

Referring now to FIG. 8A, a shoulder 22 is schematically illustrated with skin and other obstructing tissue removed so that the humerus 14 and supraspinatus tendon 28 are readily visible for purposes of better understanding exemplary procedures using the devices and methods of the current disclosure. The humerus 14 and supraspinatus tendon 28 are shown in relation to clavicle 21 and acromion 23. Further, the infraspinatus tendon 25 and teres minor tendon 27 are shown as they attach to the humerus, and as previously stated, interdigitate with the supraspinatus. The point of insertion 30 of the supraspinatus tendon 28 to humeral head 24 is also indicated and generally forms a line. The biceps tendon 29 can be seen as it extends down the arm, however, this tendon is not visible from this bursal side view on the rotator cuff of the shoulder as the biceps tendon 29 passes underneath the supraspinatus tendon and runs on the articular side of the supraspinatus tendon (beneath the tendon).

FIG. 8B illustrates a view of the articular side of the supraspinatus tendon 28 near the point of insertion 30 on the humeral head 24. This view can be seen by a surgeon through the arthroscope when positioned beneath the supraspinatus tendon. As can be seen in the illustration, the biceps tendon 29 is visible as it runs medially to the shoulder attachment. In treating the supraspinatus tendon with an implant over the bursal side of the tendon, it is preferred to not interfere with the biceps tendon by putting a staple or other attachment into this tendon. Therefore, as a first step in one method of the present disclosure, the location of the biceps tendon is marked so it is known when viewing the bursal side of the supraspinatus tendon. As illustrated in FIG. 8B, a shaft 302 of a marker assembly 300 has been inserted through the skin of the shoulder and the bursal side of the supraspinatus tendon 28 to project into the space depicted with the location being adjacent the biceps tendon 29 proximate the point of insertion 30. As depicted, the delivery assembly has not been removed nor has the arms of the marker been deployed in the illustration. When deployed the arms will abut the supraspinatus tendon on the articular side and be retained therein until sufficient force is applied to flex the arms longitudinally and be pulled through the tissue.

In some methods, a second marker system 302 is used to mark a second point medial of first marker. This is illustrated in FIG. 8C which shows a shaft 302 penetrating the bursal side of the supraspinatus tendon 28 and adjacent the biceps tendon 29 at a location medial to the first marker. As depicted, the delivery assembly has not been removed nor has the arms of the marker been deployed in the illustration. When deployed the arms will abut the supraspinatus tendon on the articular side and be retained therein until sufficient force is applied to flex the arms longitudinally.

FIG. 8D shows the shoulder as it appears on the skin surface with the two marker systems 300 inserted. The two points of insertion define a line that runs parallel to the biceps tendon under the supraspinatus tendon which indicates an area where the implant should not be located or attached to avoid interfering with the biceps tendon. FIG. 8E shows two of three incision ports that can be made relative to the marker systems 300. A first port can be located on the posterior side of the shoulder for inserting the arthroscope (not shown). A second port, the inferior lateral port 391 is made for insertion of the implant delivery system. A third port, or superior lateral port 392 is made for insertion of devices that are used to attach the implant to the tendon and bone.

A view of the bursal side of the supraspinatus tendon 28 with markers projecting therethrough is illustrated in FIG. 8F. The drawing indicates a clear visible line at the frontal margin of the supraspinatus tendon in line with the markers. Due to other tissue and ligaments in the area this is not visible to the surgeon through the arthroscope. Therefore, the markers, as placed while viewing the biceps tendon from the articular side delineate the front edge of where one would want to place the implant.

With the front edge location of the implant delineated, the next step in one method of the present disclosure is placement and attachment of the guidewire. As illustrated in FIG. 8G, with the width of the implant selected for the tendon known, the first fixed point is located a distance D plus an additional distance X in the posterior direction from the line identified by the two markers 308. In some embodiments the distance D is one-half of the width of the implant plus a distance X of about 2 mm. in the posterior direction from the line defined by the two markers 308. Further, the longitudinal distance between an implant mounted on the delivery system used and the guidewire port on the delivery shaft is known. In the illustrated method, using one representative delivery system, it is known that the longitudinal location of the first fixed point should be at the insertion point. As the implant is delivered, it will then extend proximally down the arm of the patient from the line defined by the insertion point by about 5 mm, which assures the implant extends over the point of insertion and is affixed to the humeral head 24. As illustrated in FIG. 8G, a guidewire 172 having a screw 183 for a tissue retention member is placed at the identified first fixed point.

FIG. 8H illustrates the guidewire 172 after attachment to the humeral head 24 proximate the point of insertion 30 and located posterior to the line defined by the markers 308 by a distance of one-half the width of the implant to be delivered plus about 2 mm. The implant delivery system 60 is then tracked over the guidewire 172 into the vicinity of the implant site as depicted in FIG. 8I. The delivery shaft is then extended to expose the implant distally of the sheath, which is illustrated in FIG. 8J. The entire delivery system is urged distally so that the guidewire port is proximate the first fixed point where the guidewire is attached to the bone. As indicated in FIG. 8J, this assures the proximal edge of the implant extends a distance Y beyond the point of insertion 30 and can be affixed to the humeral head 24. In some embodiments the distance Y is about 5 mm. beyond the point of insertion 30 and assures the implant can be affixed to the humeral head 24.

Referring now to FIG. 8K, the next step in one method includes deploying the implant spreader arms 120, 122 to unfurl the implant and hold it against the tendon 28. Once unfurled, the implant 50 can be rotated about the first fixed point (guidewire attachment to the bone) so that the front edge is generally parallel to the line defined by the two markers 308. As next shown in FIG. 8L, the implant 50 can be attached in multiple locations to the supraspinatus tendon 28 using staples 51. Once the medial edge is attached, the implant delivery system can be partially retracted while being used to smooth and pull the implant down and make sure it lays flat against the tendon while more staples are inserted into the tendon. In FIG. 8M, it is illustrated that the arms 120, 122 may then be closed while the implant delivery system 60 is removed from the treatment site. Referring to FIG. 8M, prior to attaching the rest of the implant, the guidewire 172 is removed in this embodiment as it is located under the edge of the implant. The guidewire delivery shaft 202 is placed over the guidewire and engages the screw head to remove the guidewire. Once removed, additional staples can be inserted in the tendon and in the bone along with removal of the markers 308.

While exemplary embodiments of the present invention have been shown and described, modifications may be made, and it is therefore intended in the appended claims and subsequently filed claims to cover all such changes and modifications which fall within the true spirit and scope of the invention.

What is claimed is:

1. A method of attaching a sheet-like implant over a tendon treatment site comprising:
    attaching a marker proximate the tendon treatment site;
    thereafter, advancing an implant delivery system to the tendon treatment site;
    deploying a sheet-like implant from the implant delivery system at the tendon treatment site;
    aligning a peripheral edge of the sheet-like implant laterally adjacent to the marker, wherein the marker does not penetrate the sheet-like implant; and
    attaching the sheet-like implant to a tendon of the tendon treatment site.

2. The method of claim 1, further comprising:
    attaching a second marker proximate the tendon treatment site.

3. The method of claim 2, further comprising:
    aligning the edge of the sheet-like implant alongside the second marker.

4. The method of claim 1, wherein the marker is attached to the tendon.

5. The method of claim 4, further comprising:
    inserting the marker through the tendon.

6. The method of claim 1, wherein the tendon is a supraspinatus tendon.

7. The method of claim 6, wherein the marker is attached adjacent to a biceps tendon.

8. The method of claim 7, wherein the marker includes a plurality of flexible arms located at a distal end of the marker.

9. The method of claim 8, wherein the plurality of flexible arms are positioned on an articular side of the supraspinatus tendon.

10. The method of claim 7, further comprising:
    inserting the marker through the supraspinatus tendon.

11. The method of claim 10, wherein the marker is inserted through the supraspinatus tendon while viewing an articular side of the supraspinatus tendon.

12. A method of attaching a sheet-like implant over a tendon treatment site comprising:
    identifying an edge of the tendon treatment site for attachment of the sheet-like implant;
    identifying a first marker attachment point at the identified edge of the tendon treatment site;
    attaching a distal end of a marker at the first marker attachment point;
    thereafter, advancing an implant delivery system to the tendon treatment site;
    deploying a sheet-like implant from the implant delivery system at the tendon treatment site; and
    attaching the sheet-like implant to a tendon of the tendon treatment site with a peripheral edge of the sheet-like implant adjacent to the marker, wherein the marker does not penetrate the sheet-like implant.

13. The method of claim 12, wherein the marker is attached to the tendon.

14. The method of claim 13, wherein the tendon is a supraspinatus tendon.

15. The method of claim 14, further comprising:
    inserting the marker through the supraspinatus tendon.

16. The method of claim 15, wherein the marker is inserted through the supraspinatus tendon while viewing an articular side of the supraspinatus tendon.

17. The method of claim 16, further comprising:
    deploying a plurality of flexible arms of the marker on the articular side of the supraspinatus tendon.

18. The method of claim 12, further comprising rotating the sheet-like implant after deployment to align the edge of the sheet-like implant with marker.

19. The method of claim 18, wherein the sheet-like implant is rotated about a fixed pivot point.

20. The method of claim 12, further comprising:
    identifying a second marker attachment point at the identified edge of the tendon treatment site spaced apart from the first marker attachment point;
    attaching a distal end of a second marker at the second marker attachment point; and
    aligning the edge of the sheet-like implant alongside the second marker, wherein the second marker does not penetrate the sheet-like implant.

* * * * *